(12) United States Patent
Padua et al.

(10) Patent No.: US 9,029,135 B2
(45) Date of Patent: May 12, 2015

(54) KANAMYCIN ANTISENSE NUCLEIC ACID FOR THE TREATMENT OF CANCER

(75) Inventors: Rose Ann Padua, Paris (FR); Christine Chomienne, Paris (FR)

(73) Assignees: Institut National de la Sante et de la Recherche Medicale (Inserm), Paris (FR); Universite Paris Diderot-Paris 7, Paris (FR)

( * ) Notice: Subject to any disclaimer, the term of this patent is extended or adjusted under 35 U.S.C. 154(b) by 0 days.

(21) Appl. No.: 13/258,173

(22) PCT Filed: Mar. 26, 2010

(86) PCT No.: PCT/EP2010/054039
§ 371 (c)(1),
(2), (4) Date: Dec. 14, 2011

(87) PCT Pub. No.: WO2010/109016
PCT Pub. Date: Sep. 30, 2010

(65) Prior Publication Data
US 2012/0076828 A1    Mar. 29, 2012

(30) Foreign Application Priority Data
Mar. 27, 2009  (EP) ..................................... 09290224

(51) Int. Cl.
| | |
|---|---|
| *C12N 15/00* | (2006.01) |
| *C12N 15/11* | (2006.01) |
| *A01N 31/04* | (2006.01) |
| *A61K 39/39* | (2006.01) |
| *C12N 15/113* | (2010.01) |
| *A61K 39/00* | (2006.01) |

(52) U.S. Cl.
CPC ............ *C12N 15/1137* (2013.01); *A61K 39/39* (2013.01); *A61K 2039/53* (2013.01); *C12N 2310/11* (2013.01); *C12N 2310/111* (2013.01)

(58) Field of Classification Search
None
See application file for complete search history.

(56) References Cited

U.S. PATENT DOCUMENTS

2005/0260619 A1    11/2005  Brousseau et al.
2006/0079470 A1 *   4/2006  Padua et al. ................... 514/44

FOREIGN PATENT DOCUMENTS

EP          1538206 A2    6/2005
WO     WO 03/090778 A2   11/2003

OTHER PUBLICATIONS

Zhou et al (DNA and Cell Biology 22(7): 475-478, 2003).*
Invitrogen Life Sciences and Services Catalog (2003), p. 280.*
Scardino et al (Cancer Res 2007;67:7028-7036, published online Jul. 17, 2007).*
http://www.drugbank.ca/molecules/6029, retrieved from the web on Mar. 4, 2013.*
www.stanford.edu/vectordb/vector_descrip/COMPLETE/PCDNA3.SEQ.html.*
Wright et al (Frontiers in Bioscience 4, d9-21, Jan. 1, 1999).*
Definition of all trans retinoic acid retrieved from the web at http://www.cancer.gov/dictionary?cdrid=367465 on Jun. 18, 2014.*
R. A. Padua et al., "PML-RARA—targeted DNA vaccine induces protective immunity in a mouse model of leukemia," Nature Medicine, vol. 9, No. 11, Nov. 2003, XP-002541189, pp. 1413-1417.
M. Robin et al., "Targeted immunotherapy in acute myeloblastic leukemia: from animals to humans," Caner Immunol Immunother (2005) 54: 933-943.

* cited by examiner

*Primary Examiner* — Richard Schnizer
(74) *Attorney, Agent, or Firm* — McDermott Will & Emery LLP

(57) ABSTRACT

The invention relates to a nucleic acid comprising a sequence complementary to a fragment of the sequence coding for the kanamycin resistance protein. This nucleic acid is useful as a DNA vaccine adjuvant, and can be used e.g. for treating cancer, for example in combination with a non-immunosuppressive inducer of tumor cell apoptosis such as all-trans retinoic acid (ATRA).

35 Claims, 13 Drawing Sheets

A.

B.

SEQUENCE LISTING

```
<160> NUMBER OF SEQ ID NOS: 23

<210> SEQ ID NO 1
<211> LENGTH: 473
<212> TYPE: DNA
<213> ORGANISM: Artificial
<220> FEATURE:
<223> OTHER INFORMATION: KanAS construct
<220> FEATURE:
<221> NAME/KEY: misc_feature
<222> LOCATION: (1)..(473)
<223> OTHER INFORMATION: Sequence complementary to a fragment of the
      sequence coding for the kanamycin resistance protein

<400> SEQUENCE: 1
agatcatcct gatcgacaag accggcttcc atccgagtac gtgctcgctc gatgcgatgt      60
ttcgcttggt ggtcgaatgg gcaggtagcc ggatcaagcg tatgcagccg ccgcattgca     120
tcagccatga tggatacttt ctcggcagga gcaaggtgag atgacaggag atcctgcccc     180
ggcacttcgc ccaatagcag ccagtccctt cccgcttcag tgacaacgtc gagcacagct     240
gcgcaaggaa cgcccgtcgt ggccagccac gatagccgcg ctgcctcgtc ttgcagttca     300
ttcagggcac cggacaggtc ggtcttgaca aaaagaaccg ggcgcccctg cgctgacagc     360
cggaacacgg cggcatcaga gcagccgatt gtctgttgtg cccagtcata gccgaatagc     420
```
ctctccaccc aagcggccgg agaacctgcg tgcaatccat cttgttcaat cat         473

<210> SEQ ID NO 2
<211> LENGTH: 573
<212> TYPE: DNA
<213> ORGANISM: Artificial
<220> FEATURE:
<223> OTHER INFORMATION: KanAS construct
<220> FEATURE:
<221> NAME/KEY: misc_feature
<222> LOCATION: (1)..(473)
<223> OTHER INFORMATION: Sequence complementary to a fragment of the
      sequence coding for the kanamycin resistance protein
<220> FEATURE:
<221> NAME/KEY: misc_feature
<222> LOCATION: (474)..(573)
<223> OTHER INFORMATION: Sequence complementary to a fragment of the
      pVax plasmid

<400> SEQUENCE: 2
agatcatcct gatcgacaag accggcttcc atccgagtac gtgctcgctc gatgcgatgt    60
ttcgcttggt ggtcgaatgg gcaggtagcc ggatcaagcg tatgcagccg ccgcattgca   120
tcagccatga tggatacttt ctcggcagga gcaaggtgag atgacaggag atcctgcccc   180
ggcacttcgc ccaatagcag ccagtccctt cccgcttcag tgacaacgtc gagcacagct   240
gcgcaaggaa cgcccgtcgt ggccagccac gatagccgcg ctgcctcgtc ttgcagttca   300
ttcagggcac cggacaggtc ggtcttgaca aaaagaaccg ggcgcccctg cgctgacagc   360
cggaacacgg cggcatcaga gcagccgatt gtctgttgtg cccagtcata gccgaatagc   420
ctctccaccc aagcggccgg agaacctgcg tgcaatccat cttgttcaat catgcgaaac   480
gatcctcatc ctgtctcttg atcagagctt gatcccctgc gccatcanat ccttggcggc   540
aagaaagcca tccantttac tttgcagggn ctt                                573

<210> SEQ ID NO 3
<211> LENGTH: 584
<212> TYPE: DNA
<213> ORGANISM: Artificial
<220> FEATURE:
<223> OTHER INFORMATION: PML-RARalphaKanAS construct
<220> FEATURE:
<221> NAME/KEY: misc_feature
<222> LOCATION: (1)..(105)
<223> OTHER INFORMATION: PML-RARalpha
<220> FEATURE:
<221> NAME/KEY: misc_feature
<222> LOCATION: (112)..(584)
<223> OTHER INFORMATION: Sequence complementary to a fragment of the
      sequence coding for the kanamycin resistance protein

<400> SEQUENCE: 3
gaggtcttcc tgcccaacag caaccacgtg gccagtggcg ccggggaggc agccattgag    60
acccagagca gcagttctga agagatagtg cccagccctc cctcgggatc cagatcatcc   120
tgatcgacaa gaccggcttc catccgagta cgtgctcgct cgatgcgatg tttcgcttgg   180
tggtcgaatg ggcaggtagc cggatcaagc gtatgcagcc gccgcattgc atcagccatg   240
atggatactt tctcggcagg agcaaggtga gatgacagga gatcctgccc cggcacttcg   300
cccaatagca gccagtccct tcccgcttca gtgacaacgt cgagcacagc tgcgcaagga   360
acgcccgtcg tggccagcca cgatagccgc gctgcctcgt cttgcagttc attcagggca   420
ccggacaggt cggtcttgac aaaaagaacc gggcgcccct gcgctgacag ccggaacacg   480
gcggcatcag agcagccgat tgtctgttgt gcccagtcat agccgaatag cctctccacc   540
caagcggccg gagaacctgc gtgcaatcca tcttgttcaa tcat            584

<210> SEQ ID NO 4
<211> LENGTH: 684
<212> TYPE: DNA
<213> ORGANISM: Artificial
<220> FEATURE:
<223> OTHER INFORMATION: PML-RARalphaKanAS construct
<220> FEATURE:
<221> NAME/KEY: misc_feature
<222> LOCATION: (1)..(105)
<223> OTHER INFORMATION: PML-RARalpha
<220> FEATURE:
<221> NAME/KEY: misc_feature
<222> LOCATION: (112)..(584)
<223> OTHER INFORMATION: Sequence complementary to a fragment of the
      sequence coding for the kanamycin resistance protein
<220> FEATURE:
<221> NAME/KEY: misc_feature
<222> LOCATION: (585)..(684)
<223> OTHER INFORMATION: Sequence complementary to a fragment of the
      pVax plasmid

<400> SEQUENCE: 4
gaggtcttcc tgcccaacag caaccacgtg gccagtggcg ccggggaggc agccattgag      60
acccagagca gcagttctga agagatagtg cccagccctc cctcgggatc cagatcatcc     120
tgatcgacaa gaccggcttc catccgagta cgtgctcgct cgatgcgatg tttcgcttgg     180
tggtcgaatg ggcaggtagc cggatcaagc gtatgcagcc gccgcattgc atcagccatg     240
atggatactt tctcggcagg agcaaggtga gatgacagga gatcctgccc ggcacttcg      300 cccaatagca gccagtccct tcccgcttca gtgacaacgt cgagcacagc tgcgcaagga     360
acgcccgtcg tggccagcca cgatagccgc gctgcctcgt cttgcagttc attcagggca     420
ccggacaggt cggtcttgac aaaaagaacc gggcgcccct gcgctgacag ccggaacacg     480
gcggcatcag agcagccgat tgtctgttgt gcccagtcat agccgaatag cctctccacc     540
caagcggccg gagaacctgc gtgcaatcca tcttgttcaa tcatgcgaaa cgatcctcat     600
cctgtctctt gatcagagct tgatcccctg cgccatcana tccttggcgg caagaaagcc     660 atccantttta ctttgcaggg nctt                                           684

<210> SEQ ID NO 5
<211> LENGTH: 105
<212> TYPE: DNA
<213> ORGANISM: Artificial
<220> FEATURE:
<223> OTHER INFORMATION: PML-RARalpha

<400> SEQUENCE: 5
gaggtcttcc tgcccaacag caaccacgtg gccagtggcg ccggggaggc agccattgag      60
acccagagca gcagttctga agagatagtg cccagccctc cctcg                    105

<210> SEQ ID NO 6
<211> LENGTH: 105
<212> TYPE: DNA
<213> ORGANISM: Artificial
<220> FEATURE:
<223> OTHER INFORMATION: PML-RARalphaAS

<400> SEQUENCE: 6
cgagggaggg ctgggcacta tctcttcaga actgctgctc tgggtctcaa tggctgcctc      60
cccggcgcca ctggccacgt ggttgctgtt gggcaggaag acctc                     105

<210> SEQ ID NO 7
<211> LENGTH: 627
<212> TYPE: DNA
<213> ORGANISM: Artificial
<220> FEATURE:
<223> OTHER INFORMATION: Fragment of pVax14
<220> FEATURE:
<221> NAME/KEY: misc_feature
<222> LOCATION: (11)..(11)
<223> OTHER INFORMATION: n is a, c, g, or t
<220> FEATURE:
<221> NAME/KEY: misc_feature
<222> LOCATION: (31)..(36)
<223> OTHER INFORMATION: HindIII restriction site
<220> FEATURE:
<221> NAME/KEY: misc_feature
<222> LOCATION: (49)..(54)
<223> OTHER INFORMATION: BamHI restriction site
<220> FEATURE:
<221> NAME/KEY: misc_feature
<222> LOCATION: (55)..(527)
<223> OTHER INFORMATION: KanAS
<220> FEATURE:
<221> NAME/KEY: misc_feature
<222> LOCATION: (528)..(627)
<223> OTHER INFORMATION: pVaxAS

<400> SEQUENCE: 7
gagacccaag nctggctagc gtttaaactt aagcttggta ccgagctcgg atccagatca      60
tcctgatcga caagaccggc ttccatccga gtacgtgctc gctcgatgcg atgtttcgct     120
tggtggtcga atgggcaggt agccggatca agcgtatgca gccgccgcat tgcatcagcc     180
atgatggata ctttctcggc aggagcaagg tgagatgaca ggagatcctg ccccggcact     240
tcgcccaata gcagccagtc ccttcccgct tcagtgacaa cgtcgagcac agctgcgcaa     300
ggaacgcccg tcgtggccag ccacgatagc cgcgctgcct cgtcttgcag ttcattcagg     360
gcaccggaca ggtcggtctt gacaaaaaga accgggcgcc cctgcgctga cagccggaac     420
acggcggcat cagagcagcc gattgtctgt tgtgcccagt catagccgaa tagcctctcc     480
acccaagcgg ccggagaacc tgcgtgcaat ccatcttgtt caatcatgcg aaacgatcct     540
catcctgtct cttgatcaga gcttgatccc ctgcgccatc anatccttgg cggcaagaaa     600
gccatccant ttactttgca gggncttl                                       627

<210> SEQ ID NO 8
<211> LENGTH: 770
<212> TYPE: DNA
<213> ORGANISM: Artificial
<220> FEATURE:
<223> OTHER INFORMATION: Fragment of pVax15
<220> FEATURE:
<221> NAME/KEY: misc_feature
<222> LOCATION: (1)..(8)
<223> OTHER INFORMATION: n is a, c, g, or t
<220> FEATURE:
<221> NAME/KEY: misc_feature
<222> LOCATION: (11)..(23)
<223> OTHER INFORMATION: n is a, c, g, or t
<220> FEATURE:
<221> NAME/KEY: misc_feature
<222> LOCATION: (24)..(29)
<223> OTHER INFORMATION: HindIII restriction site
<220> FEATURE:
<221> NAME/KEY: misc_feature
<222> LOCATION: (30)..(86)
<223> OTHER INFORMATION: Leader sequence
<220> FEATURE:
<221> NAME/KEY: misc_feature
<222> LOCATION: (87)..(191)
<223> OTHER INFORMATION: PML-RARalpha

```
<220> FEATURE:
<221> NAME/KEY: misc_feature
<222> LOCATION: (192)..(197)
<223> OTHER INFORMATION: BamHI restriction site
<220> FEATURE:
<221> NAME/KEY: misc_feature
<222> LOCATION: (198)..(670)
<223> OTHER INFORMATION: KanAS
<220> FEATURE:
<221> NAME/KEY: misc_feature
<222> LOCATION: (671)..(770)
<223> OTHER INFORMATION: pVaxAS

<400> SEQUENCE: 8
nnnnnnnntg nnnnnnnnnn nnnaagctta tggactggac ctggagggtc ttctgcttgc    60
tggctgtggc cccgggggcc cactccgagg tcttcctgcc aacagcaac cacgtggcca   120 gtggcgccgg ggaggcagcc attgagaccc agagcagcag ttctgaagag atagtgccca   180
gccctccctc gggatccaga tcatcctgat cgacaagacc ggcttccatc cgagtacgtg   240
ctcgctcgat gcgatgtttc gcttggtggt cgaatgggca ggtagccgga tcaagcgtat   300
gcagccgccg cattgcatca gccatgatgg atactttctc ggcaggagca aggtgagatg   360
acaggagatc ctgccccggc acttcgccca atagcagcca gtcccttccc gcttcagtga   420
caacgtcgag cacagctgcg caaggaacgc ccgtcgtggc cagccacgat agccgcgctg   480
cctcgtcttg cagttcattc agggcaccgg acaggtcggt cttgacaaaa agaaccgggc   540
gcccctgcgc tgacagccgg aacacggcgg catcagagca gccgattgtc tgttgtgccc   600
agtcatagcc gaatagcctc tccacccaag cggccggaga acctgcgtgc aatccatctt   660
gttcaatcat gcgaaacgat cctcatcctg tctcttgatc agagcttgat ccctgcgcc   720 atcanatcct tggcggcaag aaagccatcc antttacttt gcagggnctt              770

<210> SEQ ID NO 9
<211> LENGTH: 2999
<212> TYPE: DNA
<213> ORGANISM: Artificial
<220> FEATURE:
<223> OTHER INFORMATION: pVax1 vector
<220> FEATURE:
<221> NAME/KEY: promoter
<222> LOCATION: (137)..(724)
<223> OTHER INFORMATION: CMV promoter
<220> FEATURE:
<221> NAME/KEY: promoter
<222> LOCATION: (664)..(683)
<223> OTHER INFORMATION: T7 promoter/priming site
<220> FEATURE:
<221> NAME/KEY: misc_feature
<222> LOCATION: (696)..(811)
<223> OTHER INFORMATION: Multiple cloning site
<220> FEATURE:
<221> NAME/KEY: misc_feature
<222> LOCATION: (1226)..(2020)
<223> OTHER INFORMATION: sequence coding for the kanamycin resistance
      protein
<220> FEATURE:
<221> NAME/KEY: rep_origin
<222> LOCATION: (2320)..(2993)
<223> OTHER INFORMATION: pUC origin

<400> SEQUENCE: 9
gactcttcgc gatgtacggg ccagatatac gcgttgacat tgattattga ctagttatta    60
atagtaatca attacggggt cattagttca tagcccatat atggagttcc gcgttacata   120
acttacggta aatggcccgc ctggctgacc gcccaacgac cccgcccat tgacgtcaat   180 aatgacgtat gttcccatag taacgccaat agggactttc cattgacgtc aatgggtgga   240
```

```
ctatttacgg taaactgccc acttggcagt acatcaagtg tatcatatgc caagtacgcc      300
ccctattgac gtcaatgacg gtaaatggcc cgcctggcat tatgcccagt acatgacctt      360
atgggacttt cctacttggc agtacatcta cgtattagtc atcgctatta ccatggtgat      420
gcggttttgg cagtacatca atgggcgtgg atagcggttt gactcacggg gatttccaag      480
tctccacccc attgacgtca atgggagttt gttttggcac caaaatcaac gggactttcc      540
aaaatgtcgt aacaactccg ccccattgac gcaaatgggc ggtaggcgtg tacggtggga      600
ggtctatata agcagagctc tctggctaac tagagaaccc actgcttact ggcttatcga      660
aattaatacg actcactata gggagaccca agctggctag cgtttaaact taagcttggt      720
accgagctcg gatccactag tccagtgtgg tggaattctg cagatatcca gcacagtggc      780
ggccgctcga gtctagaggg cccgtttaaa cccgctgatc agcctcgact gtgccttcta      840
gttgccagcc atctgttgtt tgcccctccc ccgtgccttc cttgaccctg gaaggtgcca      900
ctcccactgt cctttcctaa taaaatgagg aaattgcatc gcattgtctg agtaggtgtc      960
attctattct ggggggtggg gtggggcagg acagcaaggg ggaggattgg gaagacaata     1020
gcaggcatgc tggggatgcg gtgggctcta tggcttctac tgggcggttt tatggacagc     1080
aagcgaaccg gaattgccag ctggggcgcc ctctggtaag gttgggaagc cctgcaaagt     1140
aaactggatg gctttctcgc cgccaaggat ctgatggcgc aggggatcaa gctctgatca     1200
agagacagga tgaggatcgt ttcgcatgat tgaacaagat ggattgcacg caggttctcc     1260
ggccgcttgg gtggagaggc tattcggcta tgactgggca caacagacaa tcggctgctc     1320
tgatgccgcc gtgttccggc tgtcagcgca ggggcgcccg gttcttttg tcaagaccga     1380 cctgtccggt gccctgaatg aactgcaaga cgaggcagcg cggctatcgt ggctggccac     1440
gacgggcgtt ccttgcgcag ctgtgctcga cgttgtcact gaagcgggaa gggactggct     1500
gctattgggc gaagtgccgg ggcaggatct cctgtcatct caccttgctc ctgccgagaa     1560
agtatccatc atggctgatg caatgcggcg gctgcatacg cttgatccgg ctacctgccc     1620
attcgaccac caagcgaaac atcgcatcga gcgagcacgt actcggatgg aagccggtct     1680
tgtcgatcag gatgatctgg acgaagagca tcagggctc gcgccagccg aactgttcgc     1740
caggctcaag gcgagcatgc ccgacggcga ggatctcgtc gtgacccatg gcgatgcctg     1800
cttgccgaat atcatggtgg aaaatggccg cttttctgga ttcatcgact gtggccggct     1860
gggtgtggcg gaccgctatc aggacatagc gttggctacc cgtgatattg ctgaagagct     1920
tggcggcgaa tgggctgacc gcttcctcgt gctttacggt atcgccgctc ccgattcgca     1980
gcgcatcgcc ttctatcgcc ttcttgacga gttcttctga attattaacg cttacaattt     2040
cctgatgcgg tattttctcc ttacgcatct gtgcggtatt tcacaccgca tacaggtggc     2100
acttttcggg gaaatgtgcg cggaacccct atttgtttat ttttctaaat acattcaaat     2160
atgtatccgc tcatgagaca ataaccctga taaatgcttc aataatagca cgtgctaaaa     2220
cttcattttt aatttaaaag gatctaggtg aagatccttt ttgataatct catgaccaaa     2280
atcccttaac gtgagttttc gttccactga gcgtcagacc ccgtagaaaa gatcaaagga     2340
tcttcttgag atccttttt tctgcgcgta atctgctgct tgcaaacaaa aaaaccaccg     2400
ctaccagcgg tggtttgttt gccggatcaa gagctaccaa ctctttttcc gaaggtaact     2460
ggcttcagca gagcgcagat accaaatact gtccttctag tgtagccgta gttaggccac     2520
cacttcaaga actctgtagc accgcctaca tacctcgctc tgctaatcct gttaccagtg     2580
```

```
gctgctgcca gtggcgataa gtcgtgtctt accgggttgg actcaagacg atagttaccg    2640
gataaggcgc agcggtcggg ctgaacgggg ggttcgtgca cacagcccag cttggagcga    2700
acgacctaca ccgaactgag atacctacag cgtgagctat gagaaagcgc cacgcttccc    2760
gaagggagaa aggcggacag gtatccggta agcggcaggg tcggaacagg agagcgcacg    2820
agggagcttc caggggggaaa cgcctggtat ctttatagtc ctgtcgggtt tcgccacctc    2880
tgacttgagc gtcgattttt gtgatgctcg tcagggggggc ggagcctatg gaaaaacgcc    2940
agcaacgcgg ccttttttacg gttcctgggc ttttgctggc cttttgctca catgttctt     2999
```

<210> SEQ ID NO 10
<211> LENGTH: 31
<212> TYPE: DNA
<213> ORGANISM: Artificial
<220> FEATURE:
<223> OTHER INFORMATION: primer
<400> SEQUENCE: 10

```
acgtctcttc cgcggccgct cgagtctaga g                                     31
```

<210> SEQ ID NO 11
<211> LENGTH: 32
<212> TYPE: DNA
<213> ORGANISM: Artificial
<220> FEATURE:
<223> OTHER INFORMATION: primer
<400> SEQUENCE: 11

```
acgtctcttc cggatccgag ctcggtacca ag                                    32
```

<210> SEQ ID NO 12
<211> LENGTH: 35
<212> TYPE: DNA
<213> ORGANISM: Artificial
<220> FEATURE:
<223> OTHER INFORMATION: primer
<400> SEQUENCE: 12

```
acgtctcttc ctccatggac tggacctgga gggtc                                 35
```

<210> SEQ ID NO 13
<211> LENGTH: 32
<212> TYPE: DNA
<213> ORGANISM: Artificial
<220> FEATURE:
<223> OTHER INFORMATION: primer
<400> SEQUENCE: 13

```
acgtctcttc ccgcttagtc gttggtccaa cc                                    32
```

<210> SEQ ID NO 14
<211> LENGTH: 30
<212> TYPE: DNA
<213> ORGANISM: Artificial
<220> FEATURE:
<223> OTHER INFORMATION: primer
<400> SEQUENCE: 14

```
cgaagcttat ggactggacc tggagggtct                                       30
```

<210> SEQ ID NO 15
<211> LENGTH: 28
<212> TYPE: DNA
<213> ORGANISM: Artificial

```
<220> FEATURE:
<223> OTHER INFORMATION: primer

<400> SEQUENCE: 15
cgggatcccg agggagggct gggcacta                                             28

<210> SEQ ID NO 16
<211> LENGTH: 1360
<212> TYPE: DNA
<213> ORGANISM: Clostridium tetani
<220> FEATURE:
<221> NAME/KEY: misc_feature
<222> LOCATION: (1)..(1360)
<223> OTHER INFORMATION: FrC sequence

<400> SEQUENCE: 16
atgaaaaacc ttgattgttg ggtcgacaac gaagaagaca tcgatgttat cctgaaaaag          60
tctaccattc tgaacttgga catcaacaac gatattatct ccgacatctc tggtttcaac        120
tcctctgtta tcacatatcc agatgctcaa ttggtgccgg gcatcaacgg caaagctatc        180
cacctggtta caacgaatc ttctgaagtt atcgtgcaca aggccatgga catcgaatac         240
aacgacatgt tcaacaactt caccgttagc ttctggctgc gcgttccgaa agtttctgct        300
tcccacctgg aacagtacgg cactaacgag tactccatca tcagctctat gaagaaacac        360
tccctgtcca tcggctctgg ttggtctgtt ccctgaagg gtaacaacct gatctggact         420
ctgaaagact ccgcgggcga agttcgtcag atcactttcc gcgacctgcc ggacaagttc        480
aacgcgtacc tggctaacaa atgggttttc atcactatca ctaacgatcg tctgtcttct        540
gctaacctgt acatcaacgg cgttctgatg ggctccgctg aaatcactgg tctgggcgct        600
atccgtgagg acaacaacat cactcttaag ctgaaccgtg caacaacaa caaccactac         660 gtatccatcg acaagttccg tatcttctgc aaagcactga acccgaaaga gatcgaaaaa        720
ctgtatacca gctacctgtc tatcaccttc ctgcgtgact ctggggtaa cccgctgcgt         780 tacgacaccg aatattacct gatcccggta gcttctagct ctaaagacgt tcagctgaaa        840
aacatcactg actacatgta cctgacccac gcgccgtcct acactaacgg taaactgaac        900
atctactacc gacgtctgta caacggcctg aaaatcatca tcaaacgcta cactccgaac        960
aacgaaatcg attctttcgt taaatctggt gacttcatca aactgtacgt ttcttacaac       1020
aacaacgaac acatcgttgg ttacccgaaa gacggtaacg tctttcaaca acctggacag       1080
aattctgcgt gttggttaca acgctccggg tatcccgctg tacaaaaaaa gggaagctgt       1140
taaactgcgt gacctgaaaa cctactctgt tcagctgaaa ctgtacgacg acaaaaacgc       1200
ttctctgggt ctggttggta cccacaacgg tcagatcggt aacgacccga accgtgacat       1260
cctgatcgct tctaactggt acttcaacca cctgaaagac aaaatcctgg gttgcgactg       1320
gtacttcgtt ccgaccgatg aaggttggac caacgactag                              1360

<210> SEQ ID NO 17
<211> LENGTH: 3540
<212> TYPE: DNA
<213> ORGANISM: Artificial
<220> FEATURE:
<223> OTHER INFORMATION: pVax14
<220> FEATURE:
<221> NAME/KEY: misc_feature
<222> LOCATION: (762)..(1587)
<223> OTHER INFORMATION: Flipper region, which comprises a sequence
      complementary to a fragment of the sequence coding for the
      kanamycin resistance protein
<220> FEATURE:
```

<221> NAME/KEY: misc_feature
<222> LOCATION: (1816)..(2610)
<223> OTHER INFORMATION: Sequence coding for the kanamycin resistance
      protein

<400> SEQUENCE: 17

| | | | | | |
|---|---|---|---|---|---|
| tgctggcctt | ttgctcacat | gttcttgctg | cttcgcgatg | tacgggccag | atatacgcgt | 60 |
| tgacattgat | tattgactag | ttattaatag | taatcaatta | cggggtcatt | agttcatagc | 120 |
| ccatatatgg | agttccgcgt | tacataactt | acggtaaatg | gcccgcctgg | ctgaccgccc | 180 |
| aacgaccccc | gcccattgac | gtcaataatg | acgtatgttc | ccatagtaac | gccaataggg | 240 |
| actttccatt | gacgtcaatg | ggtggagtat | ttacggtaaa | ctgcccactt | ggcagtacat | 300 |
| caagtgtatc | atatgccaag | tacgccccct | attgacgtca | atgacggtaa | atggcccgcc | 360 |
| tggcattatg | cccagtacat | gaccttatgg | gactttccta | cttggcagta | catctacgta | 420 |
| ttagtcatcg | ctattaccat | ggtgatgcgg | ttttggcagt | acatcaatgg | gcgtggatag | 480 |
| cggtttgact | cacggggatt | tccaagtctc | cacccccattg | acgtcaatgg | gagtttgttt | 540 |
| tggcaccaaa | atcaacggga | ctttccaaaa | tgtcgtaaca | actccgcccc | attgacgcaa | 600 |
| atgggcggta | ggcgtgtacg | gtgggaggtc | tatataagca | gagctctctg | gctaactaga | 660 |
| gaacccactg | cttactggct | tatcgaaatt | aatacgactc | actataggga | gacccaagct | 720 |
| ggctagcgtt | taaacttaag | cttggtaccg | agctcggatc | cagatcatcc | tgatcgacaa | 780 |
| gaccggcttc | catccgagta | cgtgctcgct | cgatgcgatg | tttcgcttgg | tggtcgaatg | 840 |
| ggcaggtagc | cggatcaagc | gtatgcagcc | gccgcattgc | atcagccatg | atggatactt | 900 |
| tctcggcagg | agcaaggtga | gatgacagga | gatcctgccc | cggcacttcg | cccaatagca | 960 |
| gccagtccct | tcccgcttca | gtgacaacgt | cgagcacagc | tgcgcaagga | acgcccgtcg | 1020 |
| tggccagcca | cgatagccgc | gctgcctcgt | cttgcagttc | attcagggca | ccggacaggt | 1080 |
| cggtcttgac | aaaaagaacc | gggcgcccct | gcgctgacag | ccggaacacg | gcggcatcag | 1140 |
| agcagccgat | tgtctgttgt | gcccagtcat | agccgaatag | cctctccacc | caagcggccg | 1200 |
| gagaacctgc | gtgcaatcca | tcttgttcaa | tcatgcgaaa | cgatcctcat | cctgtctctt | 1260 |
| gatcagagct | tgatccccctg | cgccatcaga | tccttggcgg | cgagaaagcc | atccagttta | 1320 |
| ctttgcaggg | cttcccaacc | ttaccagagg | gcgccccagc | tggcaattcc | ggttcgcttg | 1380 |
| ctgtccataa | aaccgcccag | tagaagccat | agagcccacc | gcatcccag | catgcctgct | 1440 |
| attgtcttcc | caatcctccc | ccttgctgtc | ctgccccacc | ccaccccca | gaatagaatg | 1500 |
| acacctactc | agacaatgcg | atgcaatttc | ctcattttat | taggaaagga | cagtgggagt | 1560 |
| ggcaccttcc | agggtcaagg | aaggcacggg | ggaggattgg | gaagacaata | gcaggcatgc | 1620 |
| tggggatgcg | gtgggctcta | tggcttctac | tgggcggttt | tatggacagc | aagcgaaccg | 1680 |
| gaattgccag | ctggggcgcc | ctctggtaag | gttgggaagc | cctgcaaagt | aaactggatg | 1740 |
| gctttcttgc | cgccaaggat | ctgatggcgc | agggatcaa | gctctgatca | agagacagga | 1800 |
| tgaggatcgt | ttcgcatgat | tgaacaagat | ggattgcacg | caggttctcc | ggccgcttgg | 1860 |
| gtggagaggc | tattcggcta | tgactgggca | caacagacaa | tcggctgctc | tgatgccgcc | 1920 |
| gtgttccggc | tgtcagcgca | ggggcgcccg | gttcttttg | tcaagaccga | cctgtccggt | 1980 |
| gccctgaatg | aactgcaaga | cgaggcagcg | cggctatcgt | ggctggccac | gacgggcgtt | 2040 |
| ccttgcgcag | ctgtgctcga | cgttgtcact | gaagcgggaa | gggactggct | gctattgggc | 2100 |
| gaagtgccgg | ggcaggatct | cctgtcatct | caccttgctc | ctgccgagaa | agtatccatc | 2160 |

```
atggctgatg caatgcggcg gctgcatacg cttgatccgg ctacctgccc attcgaccac    2220
caagcgaaac atcgcatcga gcgagcacgt actcggatgg aagccggtct tgtcgatcag    2280
gatgatctgg acgaagagca tcaggggctc gcgccagccg aactgttcgc caggctcaag    2340
gcgagcatgc ccgacggcga ggatctcgtc gtgacccatg gcgatgcctg cttgccgaat    2400
atcatggtgg aaaatggccg cttttctgga ttcatcgact gtggccggct gggtgtggcg    2460
gaccgctatc aggacatagc gttggctacc cgtgatattg ctgaagagct ggcggcgaa     2520 tgggctgacc gcttcctcgt gctttacggt atcgccgctc ccgattcgca gcgcatcgcc    2580
ttctatcgcc ttcttgacga gttcttctga attattaacg cttacaattt cctgatgcgg    2640
tattttctcc ttacgcatct gtgcggtatt tcacaccgca tacaggtggc acttttcggg    2700
gaaatgtgcg cggaaccct  atttgtttat ttttctaaat acattcaaat atgtatccgc    2760
tcatgagaca ataaccctga taaatgcttc aataatagca cgtgctaaaa cttcattttt    2820
aatttaaaag gatctaggtg aagatccttt ttgataatct catgaccaaa atcccttaac    2880
gtgagttttc gttccactga gcgtcagacc ccgtagaaaa gatcaaagga tcttcttgag    2940
atcctttttt tctgcgcgta atctgctgct tgcaaacaaa aaaaccaccg ctaccagcgg    3000
tggtttgttt gccggatcaa gagctaccaa ctctttttcc gaaggtaact ggcttcagca    3060
gagcgcagat accaaatact gttcttctag tgtagccgta gttaggccac cacttcaaga    3120
actctgtagc accgcctaca tacctcgctc tgctaatcct gttaccagtg ctgctgcca    3180 gtggcgataa gtcgtgtctt accgggttgg actcaagacg atagttaccg gataaggcgc    3240
agcggtcggg ctgaacgggg ggttcgtgca cacagcccag cttggagcga acgacctaca    3300
ccgaactgag atacctacag cgtgagctat gagaaagcgc cacgcttccc gaagggagaa    3360
aggcggacag gtatccggta agcggcaggg tcggaacagg agagcgcacg agggagcttc    3420 caggggggaaa cgcctggtat ctttatagtc ctgtcgggtt cgccacctct gacttgagc    3480 gtcgattttt gtgatgctcg tcagggggggc ggagcctatg aaaaacgcca gcaacgcggc    3540
```

<210> SEQ ID NO 18
<211> LENGTH: 35
<212> TYPE: PRT
<213> ORGANISM: Artificial
<220> FEATURE:
<223> OTHER INFORMATION: Immunogenic polypeptide

<400> SEQUENCE: 18

Met Arg Cys Phe Ala Trp Trp Ser Asn Gly Gln Val Ala Gly Ser Ser
1               5                   10                  15

Val Cys Ser Arg Arg Ile Ala Ser Ala Met Met Asp Thr Phe Ser Ala
            20                  25                  30

Gly Ala Arg
        35

<210> SEQ ID NO 19
<211> LENGTH: 35
<212> TYPE: PRT
<213> ORGANISM: Artificial
<220> FEATURE:
<223> OTHER INFORMATION: Immunogenic polypeptide

<400> SEQUENCE: 19

Met Phe Arg Leu Val Val Glu Trp Ala Gly Ser Arg Ile Lys Arg Met
1               5                   10                  15

Gln Pro Pro His Cys Ile Ser His Asp Gly Tyr Phe Leu Gly Arg Ser

```
                    20                  25                  30

Lys Val Arg
        35

<210> SEQ ID NO 20
<211> LENGTH: 20
<212> TYPE: PRT
<213> ORGANISM: Artificial
<220> FEATURE:
<223> OTHER INFORMATION: Immunogenic polypeptide

<400> SEQUENCE: 20

Met Thr Gly Asp Pro Ala Pro Ala Leu Arg Pro Ile Ala Ala Ser Pro
1               5                   10                  15

Phe Pro Leu Gln
        20

<210> SEQ ID NO 21
<211> LENGTH: 9
<212> TYPE: PRT
<213> ORGANISM: Artificial
<220> FEATURE:
<223> OTHER INFORMATION: Immunogenic polypeptide

<400> SEQUENCE: 21

Met Arg Asn Asp Pro His Pro Val Ser
1               5

<210> SEQ ID NO 22
<211> LENGTH: 59
<212> TYPE: PRT
<213> ORGANISM: Artificial
<220> FEATURE:
<223> OTHER INFORMATION: Immunogenic polypeptide

<400> SEQUENCE: 22

Met Pro Ala Ile Val Phe Pro Ile Leu Pro Leu Ala Val Leu Pro His
1               5                   10                  15

Pro Thr Pro Gln Asn Arg Met Thr Pro Thr Gln Thr Met Arg Cys Asn
            20                  25                  30

Phe Leu Ile Leu Leu Gly Lys Asp Ser Gly Ser Gly Thr Phe Gln Gly
        35                  40                  45

Gln Gly Arg His Gly Gly Gly Leu Gly Arg Gln
    50                  55

<210> SEQ ID NO 23
<211> LENGTH: 62
<212> TYPE: PRT
<213> ORGANISM: Artificial
<220> FEATURE:
<223> OTHER INFORMATION: Immunogenic polypeptide

<400> SEQUENCE: 23

Met Gln Phe Pro His Phe Ile Arg Lys Gly Gln Trp Glu Trp His Leu
1               5                   10                  15

Pro Gly Ser Arg Lys Ala Arg Gly Arg Ile Gly Lys Thr Ile Ala Gly
            20                  25                  30

Met Leu Gly Met Arg Trp Ala Leu Trp Leu Leu Gly Gly Phe Met
        35                  40                  45

Asp Ser Lys Arg Thr Gly Ile Ala Ser Trp Gly Ala Leu Trp
    50                  55                  60
```

KANAMYCIN ANTISENSE NUCLEIC ACID FOR THE TREATMENT OF CANCER

RELATED APPLICATIONS

This application is the U.S. National Phase under 35 U.S.C. §371 of International Application No. PCT/EP2010/054039, filed on Mar. 26, 2010, which in turn claims the benefit of European Application No. 09290224.6, filed on Mar. 27, 2009, the disclosures of which Applications are incorporated by reference herein.

The invention relates to a nucleic acid comprising a sequence complementary to a fragment of the sequence coding for the kanamycin resistance protein. This nucleic acid is useful as a DNA vaccine adjuvant, and can be used e.g. for treating cancer, for example in combination with a non-immunosuppressive inducer of tumor cell apoptosis such as all-trans retinoic acid (ATRA).

Cancer is the second more frequent cause of mortality in the US, just second to cardiovascular diseases. About 10% of these cancer deaths are caused by blood cancers such as leukaemias, lymphomas and myelomas. In the EU and US alone, there are an estimated 1.9 million people living with blood cancers. Some of these blood cancers are orphan diseases, such as acute myelogenous leukaemia (AML). Acute promyelocytic leukaemia (APL, AML type M3) is characterized by a reciprocal t(15;17) translocation fusing the Promyelocytic Leukaemia gene (PML) to the retinoic acid receptor alpha gene (RARα), and by an arrest of myeloid differentiation at the promyelocytic stage. All-trans retinoic acid (ATRA) mediated differentiation therapy is now the basis of standard treatment in patients with APL. However, despite prolonged survival obtained with the current trials combining ATRA with chemotherapy, around 10 of patients still relapse due to lack of compliance with current maintenance therapy. Therefore, novel therapeutic strategies to eradicate residual disease and improve quality of life are needed.

To date, many tumor-associated antigens have been identified and vaccination strategies to elicit immune response against these tumor antigens have been developed. Natural and recombinant cancer protein antigens contain defined immunogenic antigens at standardized levels and their efficacy depends on finding the right adjuvant and delivery system. DNA delivery, e.g. direct injection of gene expression cassettes into a living host, is a novel approach to vaccine and immunotherapy. Expression of the delivered genes may result in the specific immune activation of the host immune defenses against the expressed antigen.

The effectiveness of a vaccine strategy relies on the acquisition of an immune response that can be both humoral and cytotoxic. DNA vaccines have been shown to meet these requirements, leading to a strong and persistent cell-mediated (generation of CD8+ cytotoxic and CD4+ helper T cells) and humoral immune responses to the antigen encoded by the plasmid. The application of this type of vaccination to cancers was used first on B-Non Hodgkin's Lymphoma (B-NHL) using the idiotype of the surface immunoglobulin as the antigen against which the anti-tumoral response was elicited (Stevenson et al., 1995, Immunological Reviews 145:211-28; Syrengelas et al., 1996, Nature Medicine 2:1038-41, Rice et al., 2008, Nature Reviews 8:108-20). The protective immunity was also observed in other mouse models of lymphoma and myeloma.

However, a generalized impairment of the cellular immune system is reported in some cancer patients. On this account, the poor immune status of these patients, and in particular of APL patients, is regarded as a major obstacle for immunotherapeutic approaches to treatment of vaccination strategies alone.

Padua et al. (2003, Nature Medicine 9:1413-1417) took advantage of an APL animal model (Brown et al. 1997, Proc Natl Acad Sci USA. 94:2551-6) to test the in vivo efficacy of a DNA vaccine comprising a nucleic acid in which the PML-RARα tumor antigen is linked to tetanus toxin fragment C (FrC) sequences. Their results demonstrated that ATRA acts as an adjuvant with PML-RARα-FrC DNA vaccination to prolong survival of the APL mice. This was accompanied by an increase in CD4+ and CD8+ T-cells, RARα antibody and IFNγ production, demonstrating the induction of relevant immune responses.

WO 03/090778 further teaches that vaccine compositions that comprise (i) a non-immunosuppressive inducer of tumor cell apoptosis such as ATRA and (ii) a nucleic acid comprising a sequence that encodes an immunogenic polypeptide such as PML-RARαFrC, PML-RARαAS-FrC or ScFvBCL1-FrC rescued APL mice from relapse and death.

Therefore, therapies combining a DNA vaccination with ATRA administration constitute promising treatments of leukaemias (Padua and Chomienne, 2004, Discovery Medicine 4:41-44). There is a need in the art for the development of DNA adjuvants which are useful for increasing immune responses in cancer patients.

DESCRIPTION OF THE INVENTION

It has been surprisingly found that the KanAS sequence of SEQ ID NO: 1, which is complementary to a fragment of the sequence coding for the kanamycin resistance protein, is a highly efficient adjuvant in DNA vaccination.

More specifically, the inventors have shown that a plasmid comprising the KanAS sequence of SEQ ID NO: 1, either alone or fused with the PML-RARα tumor antigen, prolonged survival of APL mice when administered in combination with ATRA. In addition, KanAS alone extended lifespan in the MDS mice. Immune responses were measured by flow cytometry, and it was found that MDS mice treated with KanAS alone had a 3-fold increased memory T-cells compared to wild type FVB/N mice identified. Furthermore, the leukaemic stem cell progenitor population was reduced upon treatment with KanAS (approximately 25% in untreated mice versus approximately 10% in treated mice). Finally, a transient upregulation of the MyD88 transcript, which is in the pathway downstream of the Toll-like receptors (TLRs), the receptors for which DNA is one of the ligands, was observed.

Any antigen exerting an immune response may be cloned ustream or downstream of KanAS. DNA vaccination with a nucleic acid comprising KanAS is therefore applicable to all cancers, and to many other diseases requiring immune responses, including infectious diseases. The DNA vaccination strategy according to the invention may also be applicable to individuals with an inherited predisposition to cancer such as breast and colon cancer, where the oncogenes are in the germ line and inherited.

In addition, and unlike autologous vaccines, the DNA vaccines according to the invention are not vaccines specific to a given cancer condition. They neither present any danger of inducing autoimmunity to an autoantigen. Moreover, these vaccines can be manufactured by standard bacterial fermentation processes that can be readily scaled up.

KanAS Nucleic Acids According to the Invention

The invention relates to an isolated and/or purified nucleic acid comprising, or consisting of, a sequence complementary to a fragment of the sequence coding for the kanamycin resistance protein. Such a nucleic acid according to the invention is referred to as "KanAS nucleic acid". Said fragment of the sequence coding for the kanamycin resistance protein may be of any length, e.g. of at least, at most or about 50, 100, 150, 200, 250, 300, 350, 400, 450, 473 or 500 consecutive nucleotides.

In the context of the present invention, a "nucleic acid" refers to the phosphate ester polymeric form of ribonucleosides ("RNA molecules") or deoxyribonucleosides ("DNA molecules"), or any phosphoester analogs thereof, such as phosphorothioates and thioesters, in either single stranded form, or a double-stranded helix. The term "nucleic acid" includes double-stranded DNA round, inter alia, in linear (e.g., restriction fragments) or circular DNA molecules. The nucleic acid preferably corresponds to a DNA molecule.

As used herein, "isolated and/or purified" refers to a compound which is isolated and/or purified from the human or animal body, and/or from a library of compounds.

As used herein, the term "kanamycin resistance protein" refers to an enzyme capable of conferring resistance to kanamycin. Such an enzyme catalyzes the following enzymatic reaction:

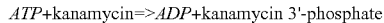

*ATP*+kanamycin=>*ADP*+kanamycin 3'-phosphate

The sequence coding for the kanamycin resistance protein may be derived from any microorganism, e.g. from *Klebsiella pneumoniae, Bacillus circulans, Escherichia coli, Enterococcus faecalis, Streptomyces fradiae, Salmonella typhimurium, Staphylococcus aureus, Acinetobacter baumannii, Streptomyces ribosidificus, Campylobacter jejuni* or *Lactococcus lactis*. Preferably, said sequence coding for the kanamycin resistance protein has a sequence consisting of nucleotides 1226 to 2020 of SEQ ID NO: 9.

The KanAs nucleic acid in accordance with the invention may further comprise a sequence complementary to a fragment of the pVax1 vector (Catalog No. V260-20, Invitrogen, Carlsbad, Calif., USA). The sequence of the pVax1 vector is shown as SEQ ID NO: 9.

Therefore, the KanAS nucleic acid in accordance to the invention may for example comprise, or consist of, a sequence complementary to a fragment of SEQ ID NO: 9, wherein said fragment of SEQ ID NO: 9 comprises at least, at most or about 50, 100, 150, 200, 250, 300, 350, 400, 450, 473 or 500 consecutive nucleotides of the nucleotides located from position 1226 to position 2020 of SEQ ID NO: 9. The fragment of SEQ ID NO: 9 may for example comprise 50 to 500, 100 to 500, 200 to 500, 300 to 500, 400 to 500 or 450 to 500 consecutive nucleotides of the nucleotides located from position 1226 to position 2020 of SEQ ID NO: 9. The KanAS nucleic acid may also correspond to a derivative of such sequences.

In a preferred embodiment, the KanAS nucleic acid comprises, or consists of:
  a sequence at least 80, 85, 90, 95, 96, 97, 98 or 99% identical to SEQ ID NO: 1 or 2;
  a fragment of at least 50, 100, 150, 200, 250, 300, 350, 400 or 450 consecutive nucleotides of SEQ ID NO: 1 or 2; or
  a derivative of SEQ ID NO: 1 or 2.

These KanAS nucleic acids preferably exhibit biological activity. As used herein, the term "biological activity" of a KanAS nucleic acid refers to the capacity to elicit an immune response in a mammal such as mouse, rat or human. Methods for measuring such a biological activity are well known in the art. For example, the methods disclosed in Padua et al. (2003, Nature Medicine 9:1413-1417) may be used. In one preferred embodiment, the biological activity of the KanAS nucleic acid is measured by assessing its capacity to prolong survival in mouse models of APL or MDS (hereafter "APL mice" or "MDS mice"), when administered in combination with ATRA (see Examples 2 and 3 of the instant patent application).

By a nucleic acid having a sequence at least, for example, 95% "identical" to a query sequence of the present invention, it is intended that the sequence of the nucleic acid is identical to the query sequence except that the sequence may include up to five nucleotide alterations per each 100 nucleotides of the query sequence. In other words, to obtain a nucleic acid having a sequence at least 95% identical to a query sequence, up to 5% (5 of 100) of the nucleotides of the sequence may be inserted, deleted, or substituted with another nucleotide.

The term "derivative" includes fragments, homologues, mutants and naturally-occurring variants such as allelic variants, splice variants or variants obtained through proteolytic processing. Derivatives consisting of an amino acid sequence "at least 80, 85, 90, 95, 96, 97, 98 or 99% identical" to a reference sequence may comprise mutations such as deletions, insertions and/or substitutions compared to the reference sequence. In case of substitutions, the derivative consisting of an amino acid sequence at least 80, 85, 90, 95, 96, 97, 98 or 99% identical to a reference sequence may correspond to a homologous sequence derived from another species than the reference sequence. The substitution may correspond to a conservative substitution as indicated in the table below.

| Conservative substitutions | Type of Amino Acid |
|---|---|
| Ala, Val, Leu, Ile, Met, Pro, Phe, Trp | Amino acids with aliphatic hydrophobic side chains |
| Ser, Tyr, Asn, Gln, Cys | Amino acids with uncharged but polar side chains |
| Asp, Glu | Amino acids with acidic side chains |
| Lys, Arg, His | Amino acids with basic side chains |
| Gly | Neutral side chain |

In one specific embodiment, the KanAS nucleic acid comprises, or consists of, an antisense sequence encoding at least one peptide or polypeptide, wherein said antisense sequence is complementary to a fragment of the sequence coding for the kanamycin resistance protein.

The KanAS nucleic acid may further comprise a sequence that encodes at least one immunogenic polypeptide. Said sequence that encodes at least one immunogenic polypeptide may for example correspond to the sequence of a nucleic acid encoding an immunogenic polypeptide in accordance with WO 03/090778.

In one embodiment, the immunogenic polypeptide corresponds to a tumor antigen. Thus, according to this embodiment, the KanAS nucleic acid according to the invention comprises a sequence complementary to a fragment of the sequence coding for the kanamycin resistance protein and a sequence that codes for a tumor antigen. These two sequences may be fused in frame, i.e. lead to the expression of a fusion protein between the tumor antigen and a peptide or polypeptide encoded by the sequence complementary to a fragment of the sequence coding for the kanamycin resistance protein. The tumor antigen may be fused to the N- or C-terminal end of the peptide or polypeptide encoded by the sequence complementary to a fragment of the sequence coding for the kanamycin resistance protein.

Among tumor antigens that can be advantageously used, one can cite human PML (Promyelocytic Leukaemia gene)-RARα (retinoic acid receptor alpha gene), acute myeloid leukaemia 1/Eight-Twenty one (AML1/ETO), core binding factor beta/muscle myosin heavy chain (CBF beta/MYH11), ets-like gene/platelet derived growth factor receptor beta (Tel-PDGF), promyelocytic leukaemia zing finger/retinoic acid receptor alpha (PLZF-RAR), myeloid/lymphoid (MLL) fusions, of which there are 40 potential partners, ets-like gene/acute myeloid leukaemia 1 (AML-1-ETO), breakpoint cluster region/Abelson (BCR-ABL), TEL-AML1, E2A-PBX, MLL-AF4 and oncogenes activated by mutations such as the RAS genes.

In a specific embodiment of the invention, the tumor antigen is PML-RARα. The term "PML-RARα antigen" denotes a fusion protein resulting from the t(15;17) chromosomal translocation described in Thé et al. (1990, Nature 347:558-61). The PML-RARα antigen may for example comprise, or consist of, the sequence of SEQ ID NO: 5, or a derivative thereof.

In a preferred embodiment, the KanAS nucleic acid comprises, or consists of:
  a sequence at least 80, 85, 90, 95, 96, 97, 98 or 99% identical to the PML-RARαKanAS sequence of SEQ ID NO: 3 or SEQ ID NO: 4;
  a fragment of at least 50, 100, 150, 200, 250, 300, 350, 400, 450, 500 or 550 consecutive nucleotides of SEQ ID NO: 3 or SEQ ID NO: 4; or
  a derivative of SEQ ID NO: 3 or SEQ ID NO: 4.

These KanAS nucleic acids preferably exhibit biological activity.

Alternatively, the sequence encoding the immunogenic polypeptide is "non-specific" of cancer condition. In the frame of this embodiment, any immune response enhancer may be appropriate, even though the sequence does not include a tumor antigen.

Immunogenic polypeptide that are "non-specific" of cancer condition are disclosed e.g. in WO 03/090778 and include PML-RARαAS or ScFvBCL1. The "non-specific" immunogenic polypeptide may for example be encoded by a sequence comprising or consisting of the sequence of SEQ ID NO: 6 (PML-RARαAS), or derivatives thereof. The sequence that encodes said "non-specific" immunogenic polypeptide may also be selected from the group consisting of a tetanus toxin fragment C (FrC) (SEQ ID NO: 16), a cholera toxin (CT) sequence, a E. coli heat-labile toxin (LT) sequence, a pertussis toxin (PT) sequence, a Clostridium difficile toxin A sequence, and immunogenic fragments thereof.

Immunogenic polypeptides can easily be identified by the skilled in the art using appropriate softwares. For example, characterizing the hydrophobic character (e.g. by analyzing hydrophobicity plots) of polypeptides allows predicting whether they are immunogenic. Softwares for characterizing the hydrophobic character of a polypeptide include, e.g. those based on the use of the Kyte-Doolittle or the Hopp-Woods algorithm. The Kyte-Doolittle algorithm is a widely applied scale for delineating hydrophobic character of a protein. Regions with values above 0 are hydrophobic in character. The Hopp-Woods algorithm was designed for predicting potentially antigenic regions of polypeptides. Values greater than 0 are hydrophilic, and thus likely to be exposed on the surface of a folded protein.

In a specific embodiment, the immunogenic polypeptide is selected from the group consisting of any one of SEQ ID Nos. 18-23. These immunogenic polypeptides were identified using the above softwares for characterizing the hydrophobic character of a polypeptide.

The invention further pertains to a vector comprising a KanAS nucleic acid, on which the KanAS nucleic acid is placed under the control of signals (e.g. a promoter, a terminator and/or an enhancer) allowing the transcription of the KanAS nucleic acid. The vector preferably corresponds to DNA vaccination vector, i.e. a vector specifically designed for the development of DNA vaccines. The DNA vaccination vector may correspond to or be derived from, e.g. the pVax1 (Invitrogen, Carlsbad, Calif., USA) or the pCDNA$_3$ (Invitrogen, Carlsbad, Calif., USA) expression vector. The vector may further comprise a resistance gene conferring resistance to an antibiotic such as ampicillin or kanamycin. Alternatively, the vector does not comprise any gene conferring resistance to an antibiotic.

Therapeutic Uses of the KanAS Nucleic Acids According to the Invention

It has been found that the KanAS nucleic acid described hereabove is useful in DNA vaccination, in particular as an adjuvant. Such a KanAS nucleic acid elicits the immune response and can thus be used to treat various diseases in which an enhanced immune response is sought for, such as e.g. infectious diseases and cancers. Therefore, the invention pertains to a KanAS nucleic acid according to the invention for use in DNA vaccination (e.g. as an aduvant), and/or for use in the treatment or prevention of cancers, benign tumors or infectious diseases.

As used herein, the term "cancer" refers to any type of malignant (i.e. non benign) tumor.

The malignant tumor preferably corresponds to a blood (or haemotological) cancer such as a leukaemia, a lymphoma or a myeloma. Such blood cancers include e.g. acute promyelocytic leukaemia (APL), acute myeloid leukaemia (AML), lymphoid or myeloid leukaemia, chronic lymphocytic leukaemia (CLL), chronic myelogenous leukaemia (CML), myelomonocytic leukaemia (CMML), childhood acute lymphoblastic leukaemia (ALL), myelodysplastic syndrome (MDS), Hodgkin lymphoma (HD), non-Hodgkin lymphoma (NHL) and multiple myeloma (MM).

Alternatively, the tumor may correspond to a solid tumor such as e.g. a carcinoma, an adenocarcinoma, a sarcoma, a malignant melanoma, a mesothelioma or a blastoma. In a specific embodiment, the solid tumor corresponds to a pancreatic cancer, a lung cancer, a breast cancer, a colon cancer or a colorectal cancer.

The term "infectious disease" includes diseases caused by various organisms such as bacteria, mycoplasmas, protozoa, fungi and viruses (e.g. HIV, hepatitis viruses, in particular HBV or HCV).

By "treatment" is meant a therapeutic use (i.e. on a patient having a given disease) and by "preventing" is meant a prophylactic use (i.e. on an individual susceptible of developing a given disease). The term "treatment" not only includes treatment leading to complete cure of the diseases, but also treatments slowing down the progression of the disease and/or prolonging the survival of the patient.

In the frame of cancer treatments, the KanAS nucleic acid according to the invention is preferably for simultaneous or sequential use in combination with a non-immunosuppressive inducer of tumor cell apoptosis. In other terms, The nucleic acid and the non-immunosuppressive inducer of tumor cell apoptosis may be administered concurrently, i.e. simultaneously in time, or sequentially, i.e. at different times during the course of a common treatment schedule of a patient. However, the KanAS nucleic acid in accordance with the invention is also efficient when used alone (see e.g. Example 3).

"Apoptosis" refers to a form of cell death that exhibits stereotypic morphological changes. Apoptosis can be measured, e.g., by the propidium iodide flow cytometry assay described in Dengler et al. (1995, Anticancer Drugs. 6:522-32), or by the in situ terminal deoxynucleotidyl transferase and nick translation assay (TUNEL analysis) described in Gorczyca (1993, Cancer Res. 53:1945-51).

"Non-immunosuppressive inducers of tumor cell apoptosis" are well-known in the art. The non-immunosuppressive inducer of tumor cell apoptosis may for example correspond to a retinoid compound, an arsenic-related compound, CD437 and other differentiation and apoptosis inducers, compounds activating CD44 such as antibodies and hyaluronic acid, hematopoietic growth and differentiation factors, 5-azacytidine and other demethylating agents, farnesyl transferase inhibitors (FTI), histone deacetylate inhibitors (HDACi), small molecules such as Imatinib, BH3 mimetic inhibitors such as ABT 737, and RAC1 inhibitors.

"Retinoid compounds" refer to vitamin A derivatives and include e.g. retinoic acid (RA), all-trans retinoic acid (ATRA), 9-cis RA, 4-HPPR, 13-cis RA and synthetic analogs of retinoic acid such as AM 580. Preferably, the retinoid compound corresponds to ATRA or AM 580.

"Arsenic-related compounds" denotes any compound that, just as arsenic, is a phosphatase inhibitor or is capable of creating covalent bonds by dithiol group binding. Such compounds include, e.g. arsenic and arsenic trioxide.

In a preferred embodiment, the non-immunosuppressive inducer of tumor cell apoptosis has adjuvant activity towards the biological response elicited by said nucleic acid. "Adjuvant activity" is defined herein as an effect achieved by the combination of two components that is greater than the effect of either of the two components alone.

The KanAS nucleic acid according to the invention, optionally combined with a non-immunosuppressive inducer of tumor cell apoptosis, may be administered in combination with a least one anti-cancer drug such as e.g. 5-azacytidine (Vidaza™) or decitabine (simultaneously or sequentially).

In the frame of cancer treatments, the KanAS nucleic acid according to the invention preferably comprises a sequence that encodes a tumor antigen. Most preferably, the tumor antigen is specific to the cancer to be treated. Examples of antigens useful for cancer therapy include PML-RARα for the treatment of acute promyelocytic leukaemia (APL) and myelodysplastic syndrome (MDS), AML1-ETO for the treatment of acute myeloid leukaemia (AML) type M2, CBF beta-MYH11 in AML type M4 Eosinophilia, Tel-PDGF for chronic myelomonocytic leukaemia (CMML), PLZF-RARα in variant APL, MLL fusions in various lymphoid or myeloid leukaemia, TEL-AML-1, E2A-PBX, MLL-AF4 or oncogenes activated by mutations such as the RAS genes for childhood acute lymphoblastic leukaemia, and BCR-ABL for the treatment of chronic myelogenous leukaemia or childhood acute lymphoblastic leukemia (ALL).

The invention also contemplates a method for eliciting an immune response and/or for treating or preventing cancers or infections diseases comprising the step of administering an effective amount of a KanAs nucleic acid in accordance with the invention, optionally in combination with a non-immunosuppressive inducer of tumor cell apoptosis, to an individual in need thereof.

By "effective amount" is meant an amount sufficient to achieve a concentration of peptide which is capable of preventing, treating or slowing down the disease to be treated. Such concentrations can be routinely determined by those of skilled in the art. The amount of the compound actually administered will typically be determined by a physician, in the light of the relevant circumstances, including the condition to be treated, the chosen route of administration, the actual compound administered, the age, weight, and response of the individual patient, the severity of the patient's symptoms, and the like. It will also be appreciated by those of stalled in the art that the dosage may be dependent on the stability of the administered peptide.

By "individual in need thereof" is meant an individual suffering from or susceptible of suffering from the disease to be treated or prevented. The individuals to be treated in the frame of the invention are preferably human individuals. However, the veterinary use of KanAS nucleic acids is also contemplated by the present invention.

Pharmaceutical Compositions According to the Invention

The KanAS nucleic acids according to the invention are useful as drugs (medicaments). Therefore, an aspect of the invention is directed to a pharmaceutical composition comprising a KanAS nucleic acid as described hereabove, and/or an expression vector comprising such a KanAS nucleic acid in a physiologically acceptable carrier. Such pharmaceutical compositions preferably correspond to vaccine compositions.

The term "physiologically acceptable carrier" is meant to encompass any carrier, which does not interfere with the effectiveness of the biological activity of the active ingredient and that is not toxic to the host to which is administered. Suitable physiologically acceptable carriers are well known in the art and are described for example in Remington's Pharmaceutical Sciences (Mack Publishing Company, Easton, USA, 1985), which is a standard reference text in this field.

In a preferred embodiment, the pharmaceutical composition further comprises a non-immunosuppressive inducer of tumor cell apoptosis such as e.g. arsenic, arsenic trioxide, all-trans retinoic acid (ATRA), 9-cis RA, 4-HPPR, 13-cis RA or AM 580. Such pharmaceutical compositions are especially useful for the treatment of cancers. Preferably, the non-immunosuppressive inducer of tumor cell apoptosis has adjuvant activity towards the biological response elicited by the KanAS nucleic acid and/or the expression vector comprising the KanAS nucleic acid. Most preferably, the KanAS nucleic acid according to the invention comprises a sequence that encodes a tumor antigen, for example a tumor antigen specific to the cancer to be treated.

The pharmaceutical composition may further comprise at least one anti-cancer drug such as e.g. 5-azacytidine (Vidaza™) or decitabine.

The invention further pertains to a combination of:
(i) a first pharmaceutical composition comprising a KanAS nucleic acid according to the invention and/or an expression vector comprising such as KanAS nucleic acid in a physiologically acceptable carrier; and
(ii) a second pharmaceutical composition comprising a non-immunosuppressive inducer of tumor cell apoptosis such as e.g. arsenic, arsenic trioxide, all-trans retinoic acid (ATRA), 9-cis RA, 4-HPPR, 13-cis RA or AM 580 in a physiologically acceptable carrier; and, optionally
(iii) an anticancer drug such as 5-azacytidine (Vidaza™) or decitabine.

Such a combination may for example correspond to a kit. The kit may further comprise instructions for the use in the treatment of cancer. Alternatively, the first and second pharmaceutical compositions may be commercialized separately.

The first and second pharmaceutical compositions of the combination according to the invention may either be intended to be administered sequentially (i.e. at different times during the course of a common treatment schedule), or be intended to be administered simultaneously.

In a preferred embodiment, the first pharmaceutical composition of the combination according to the invention comprises a KanAS nucleic acid comprising a sequence that encodes a tumor antigen, for example a tumor antigen specific to the cancer to be treated (e.g. PML-RARα, AML1-ETO, CBF beta-MYH11, Tel-PDGF, PLZF-RARα, MLL fusions, TEL-AML-1 or BCR-ABL). Most preferably, the non-immunosuppressive inducer of tumor cell apoptosis has adjuvant activity towards the biological response elicited by the KanAS nucleic acid and/or the expression vector comprising the KanAS nucleic acid.

The KanAS nucleic acids and/or vectors comprising such a KanAS nucleic acid according to the invention may be administered in a naked form, free from any delivery vehicles. To this end, the nucleic acid is simply diluted in a physiologically acceptable solution such as sterile saline or sterile buffered saline, with or without a carrier. When present, the carrier is preferably isotonic, hypotonic, or weakly hypertonic, and has a relatively low ionic strength, such as provided by a sucrose solution, e.g., a solution containing 20% sucrose.

Alternatively, the KanAS nucleic acids and/or vectors comprising such a KanAS nucleic acid according to the invention, or the nucleic acid of the vaccine compositions, combinations or kits of the invention may be administered in association with agents that assist in cellular uptake. Examples of such agents are (i) chemicals that modify cellular permeability, such as bupivacaine (see, e.g., WO 94/16737), (ii) liposomes or viral particles for encapsulation of the polynucleotide, or (iii) cationic lipids or silica, gold, or tungsten microparticles which associate themselves with the polynucleotides.

Anionic and neutral liposomes are well-known in the art (see, e.g., Liposomes: A Practical Approach, RPC New Ed, IRL press, 1990), for a detailed description of methods for making liposomes) and are useful for delivering a large range of products, including polynucleotides.

Cationic lipids are also known in the art and are commonly used for gene delivery. Such lipids include Lipofectin Tm also known as DOTMA (N-[1-(2,3-dioleyloxy)propyls N, N,N-trimethylammonium chloride), DOTAP (1,2-bis(oleyloxy)-3 (trimethylammonio) propane), DDAB (dimethyldioctadecyl-ammonium bromide), DOGS (dioctadecylamidologlycyl spermine) and cholesterol derivatives such as DC-Chol (3 beta-(N—(N',N'-dimethyl aminomethane)-carbamoyl)cholesterol). A description of these cationic lipids can be found in EP 187,702, WO 90/11092, U.S. Pat. No. 5,283,185, WO 91/15501, WO 95/26356, and U.S. Pat. No. 5,527,928. Cationic lipids for gene delivery are preferably used in association with a neutral lipid such as DOPE (dioleyl phosphatidylethanolamine), as described in WO 90/11092 as an example.

Formulation containing cationic liposomes may optionally contain other transfection-facilitating compounds. A number of them are described in WO 93/18759, WO 93/19768, WO 94/25608, and WO 95/02397. They include spermine derivatives useful for facilitating the transport of DNA through the nuclear membrane (see, for example, WO 93/18759) and membrane permeabilizing compounds such as GALA, Gramicidine S, and cationic bile salts (see, for example, WO 93/19768).

Gold or tungsten microparticles may be used for gene delivery, as described in WO 91/00359 or WO 93/17706. The microparticle-coated polynucleotide is injected via intradermal or intraepidermal routes using a needleless injection device ("gene gun"), such as those described in U.S. Pat. No. 4,945,050, U.S. Pat. No. 5,015,580, and WO 94/24263. Otherwise, naked DNA can be directly injected, i.e. intramuscularly.

The amount of DNA to be used in a pharmaceutical composition depends, e.g., on the strength of the promoter used in the DNA construct, the immunogenicity of the expressed tumor antigen, the condition of the mammal intended for administration (e.g., weight or age), the mode of administration, and the type of formulation. In general, a therapeutically effective dose from about 1 µg to about 8 mg, preferably about 1 µg to about 1 mg (Graham, B. S. et al. J. Infect. Dis. 194, 1650-1660(15 Dec. 2006)), preferably, from about 10 µg to about 800 µg and, more preferably, from about 25 µg to about 250 µg, can be administered to human adults. The administration can be achieved in a single dose or repeated at intervals.

The route of administration is any conventional route used in the field of DNA vaccination. As general guidance, a nucleic acid of the invention may be administered via a parenteral route, e.g., by an intradermal, intraepidermal, or intramuscular route. The choice of administration route depends on the formulation that is selected. A polynucleotide formulated in association with bupivacaine is advantageously administered into muscles. When a neutral or anionic liposome or a cationic lipid, such as DOTMA or DC-Chol, is used, the formulation can be advantageously injected via intramuscular or intradermal routes. A polynucleotide in a naked form can advantageously be administered via the intramuscular, intradermal, or subcutaneous routes. In addition electroporation can be developed to improve delivery of DNA to muscle (Mir et al. 1999, Proc Natl Acad Sci USA. 96:4262-7).

In the frame of cancer treatments, the nucleic acid therapy is preferably combined with administration of a non-immunosuppressive inducer of tumor cell apoptosis, such as arsenic, low dose chemotherapy or all-trans retinoic acid or other retinoic acid compounds, as 9-cis RA, 4 HPR, 13 cis RA, CD437 and other differentiation and apoptosis inducers, activation of CD44 by antibodies or hyaluronic acid, hematopoietic growth and differentiation factors. A patient is administered with this inducer that is either present in the same vaccine composition as the nucleic acid of the invention, or is present in the form of a separate composition. In the latter, the route of administration may be identical or different to the route of administration used for the nucleic acid. For instance, one may deliver the nucleic acid composition through intradermal or intramuscular routes, whereas the inducer is administered orally.

All references cited herein, including journal articles or abstracts, published patent applications, issued patents or any other references, are entirely incorporated by reference herein, including all data, tables, figures and text presented in the cited references.

Although having distinct meanings, the terms "comprising", "having", "containing' and "consisting of" have been used interchangeably throughout this specification and may be replaced with one another.

The invention will be further evaluated in view of the following examples and figures.

ATRA+pCDNA₃PML-RARαASFrC (n=12) (VVACS04); Row 4: ATRA+pVaxPML-RARαFrC (n=12) (VVACS01). Row 5: ATRA (n=32). Row 6: placebo+DNA (pCDNA₃PML-RARαFrC) (n=11) (VVACS01). Row 7: Placebo (n=10).

Figure 3:
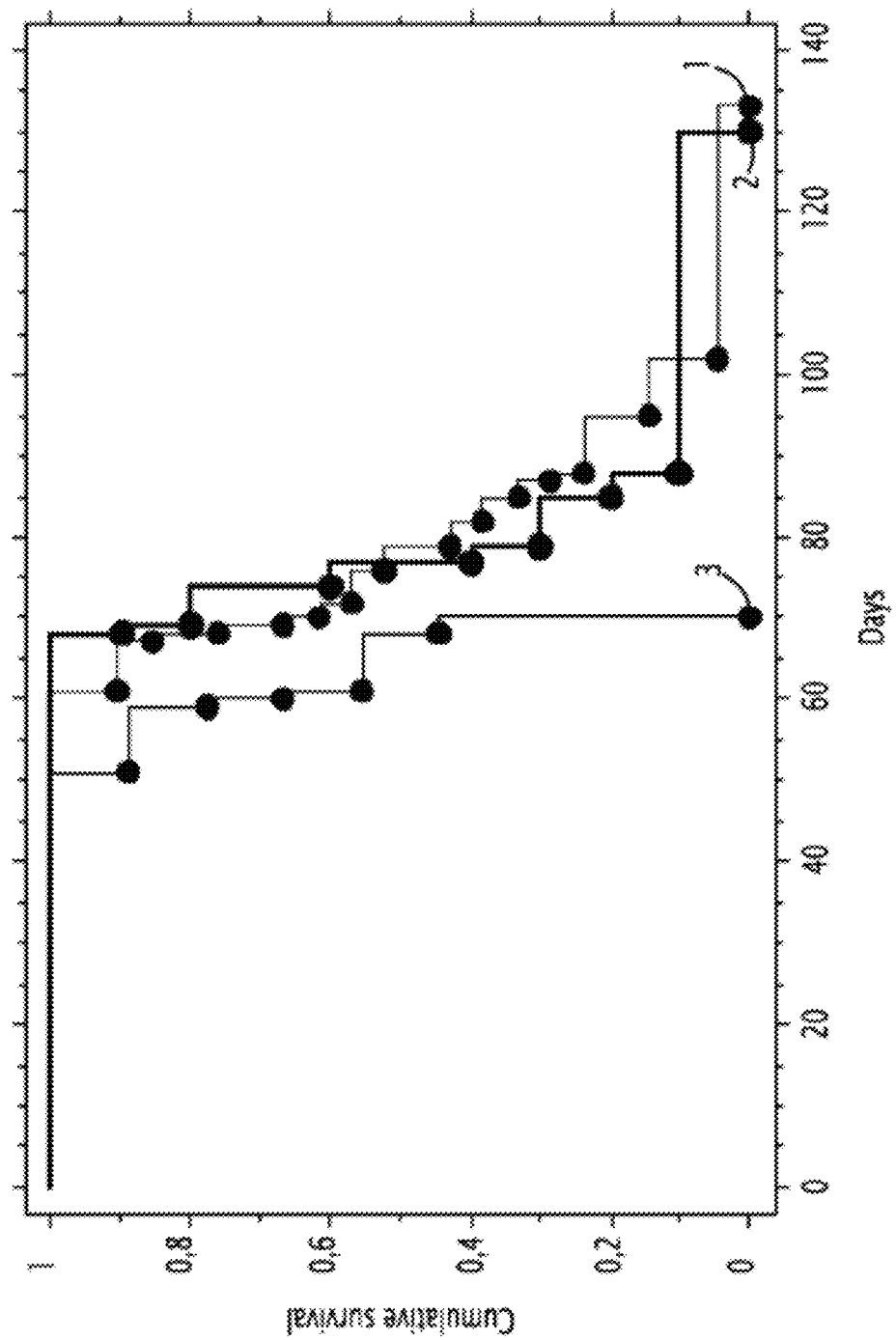

FIG. 3 shows that the pVax15 nucleic acid, which comprises the PML-RARαKanAS nucleic acid of SEQ ID NO: 3, extends lifespan in an APL mouse model. Row 1: ATRA+pCDNA₃PML-RARαFrC (n=21) (VVACS01); Row 2: ATRA+pVaxPML-RARαKanAS (n=10) (pVax15, VVACS03); Row 3: ATRA (n=9).

Figure 4:
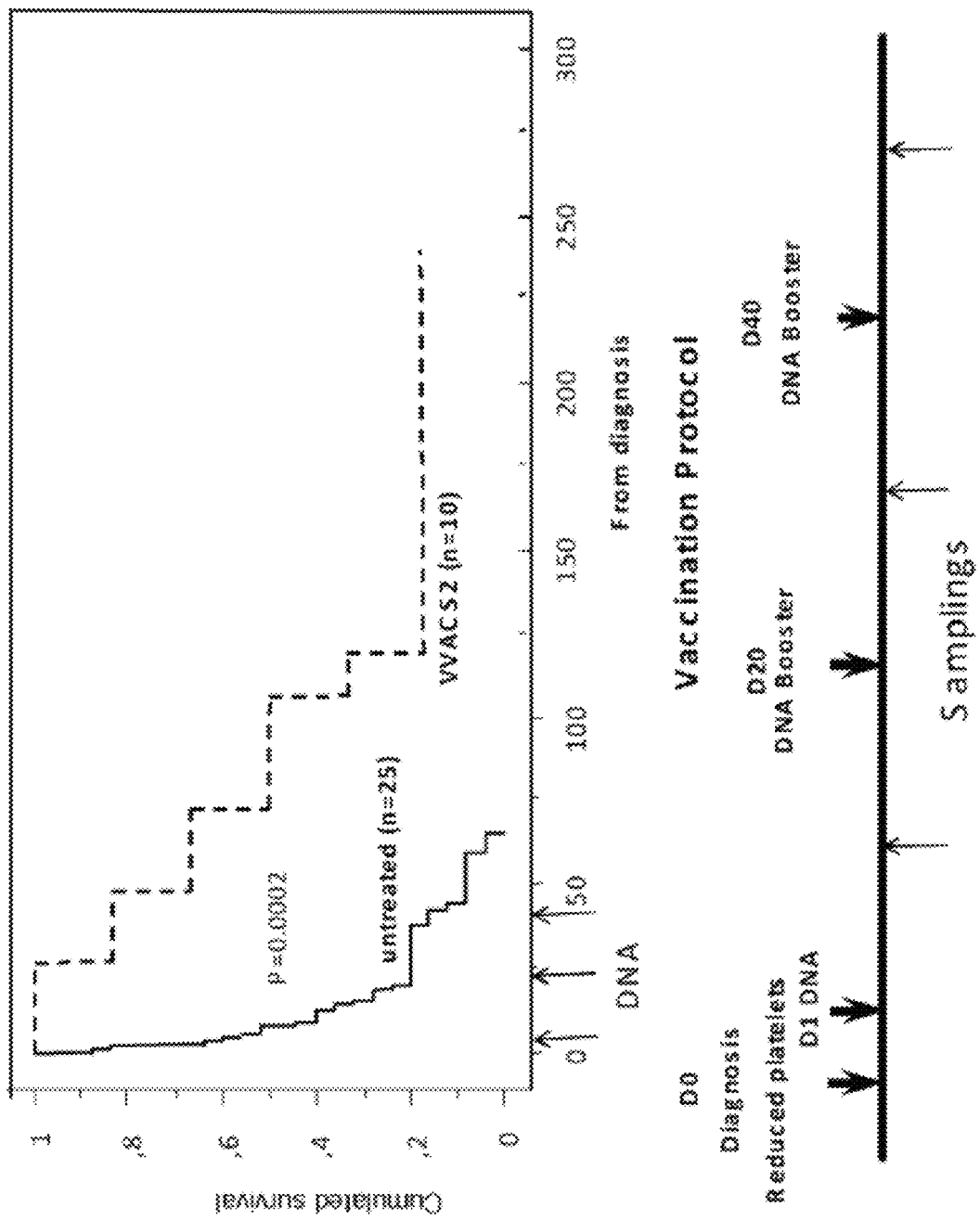

FIG. 4 shows that the pVax14 (VVACS02) nucleic acid, which comprises the KanAS nucleic acid of SEQ ID NO: 1, extends lifespan in a MDS (myelodysplastic syndrome) mouse model. Row 1: pVaxKanAS (pVax14, VVACS02) (n=6); Row 2: No treatment (n=25). P=0.0002

Figure 5:
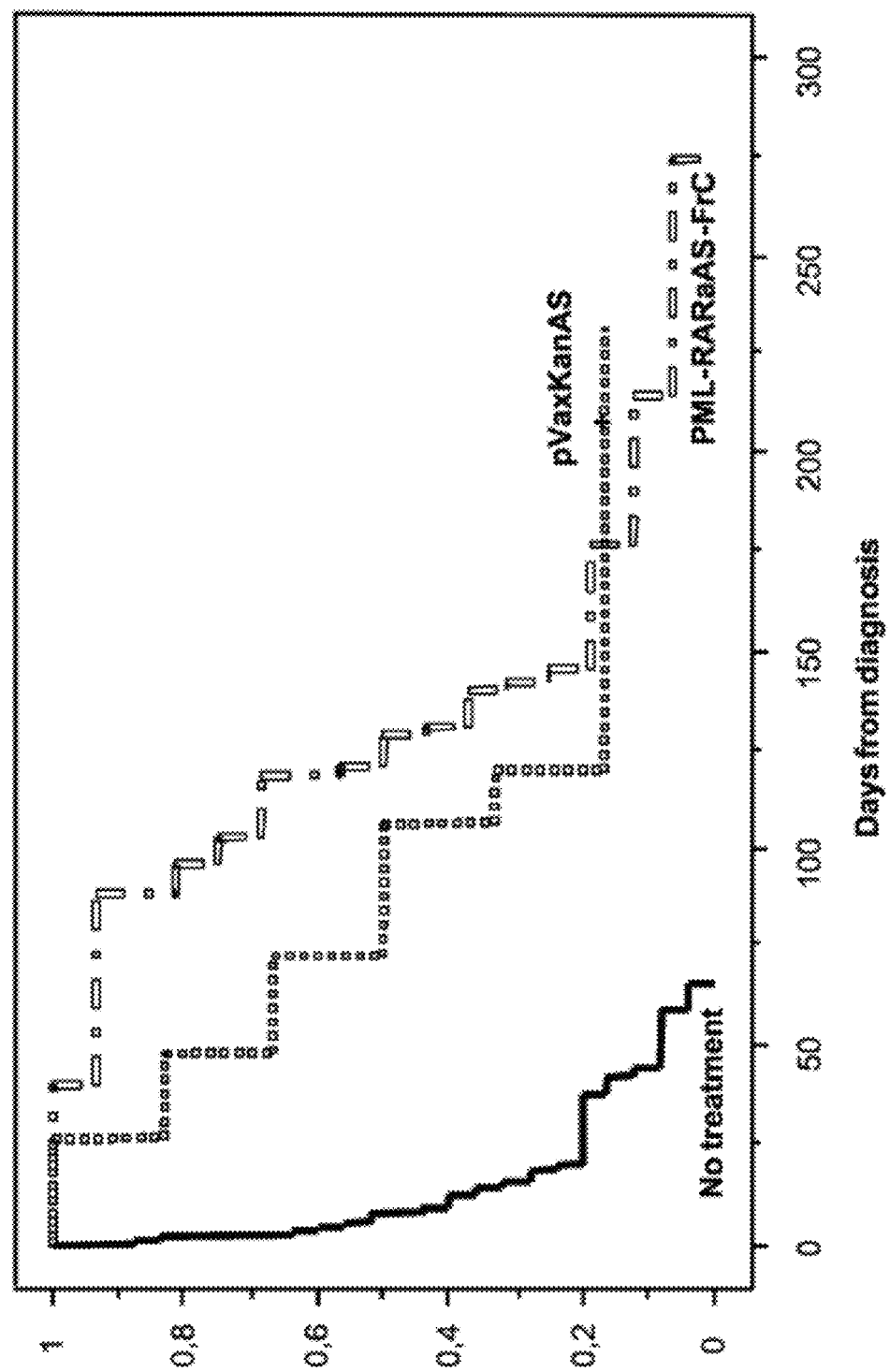

FIG. 5 shows that the pVax14 nucleic acid, which comprises the KanAS nucleic acid of SEQ ID NO: 1, extends lifespan in a MDS mouse model. pVaxKanAS (n=10) (pVax14, VVACS02); PML-RARaAS-FrC (n=16) (VVACS04); No treatment: n=25. P values: No treatment vs. PML-RARaAS-FrC<0.0001; No treatment vs. pVaxKanAS=0.0002; PML-RARaAS-FrC vs. pVaxKanAS=0.3648.

Figure 6:
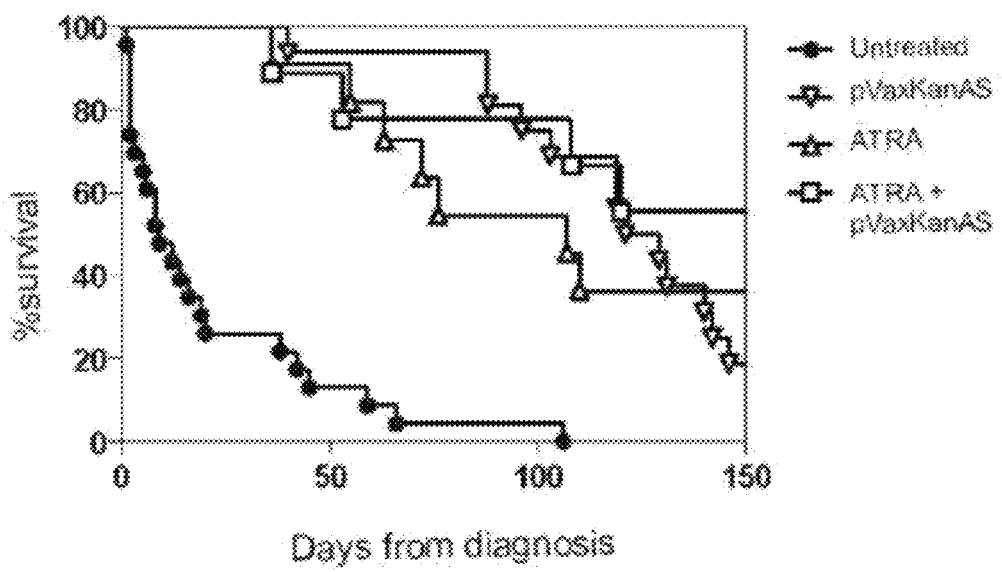

FIG. 6 shows that pCDNA3PMLRARαASFrC extends lifespan of MDS mice. pCDNA3PMLRARαASFrC (n=16) (VVACS04); No treatment: n=26; ATRA: 0=11; ATRA+pCDNA3PMLRARαASFrC (n=9) (VVACS04). Log-rank P values: pCDNA3PMLRARαASFrC (VVACS04), ATRA or ATRA+DNA vs untreared=<0.0001; pCDNA3PML-RARαASFrC (VVACS04) vs. ATRA=0.9994; pCDNA3PML-RARαASFrC (VVACS04) vs. ATRA+pCDNA3PML-RARαASFrC (VVACS04)=0.1957; ATRA vs. pCDNA3PML-RARαASFrC+ATRA=0.3834.

Figure 7:

FIG. 7 shows that vaccination of mice with the pVax14 nucleic acid, which comprises the KanAS nucleic acid of SEQ ID NO: 1, results in an increase of the CD4⁺ CD44$^{hi}$ CD62L$^{lo}$ memory T cell population. D15, D33 and D183 indicate the days from diagnosis of MDS.

Figure 8:
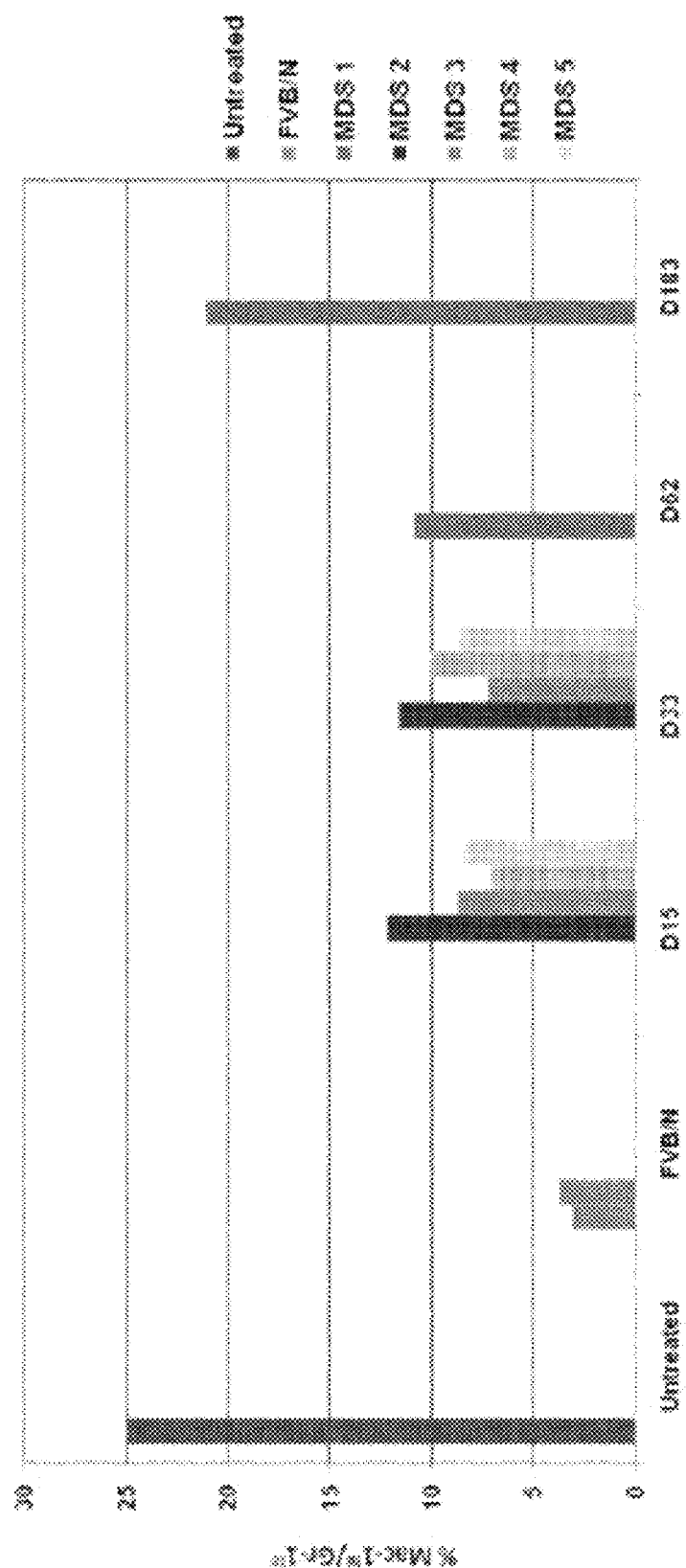

FIG. 8 shows that vaccination of mice with the pVax14 nucleic acid, which comprises the KanAS nucleic acid of SEQ ID NO: 1, enables maintenance of the Mac-2$^{hi}$/Gr1$^{lo}$ leukaemic initiating cell population at a stable level. D15, D33 and D183 indicate the days from diagnosis of MDS.

Figure 9:
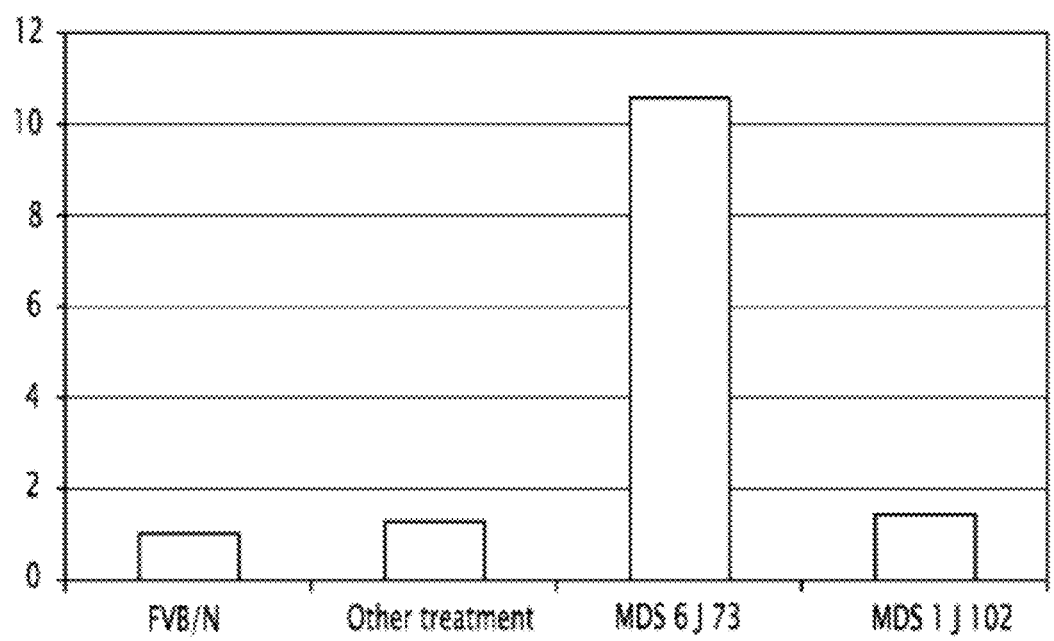

FIG. 9 shows that DNA Vaccination up-regulates MyD88, which is in the signaling pathway downstream of the Toll-like receptors (TLRs), the receptors for which DNA is the ligand. Thus the increased expression of MyD88 seen upon DNA vaccination indicates that there is a transient activation of TLRs.

Figure 10:
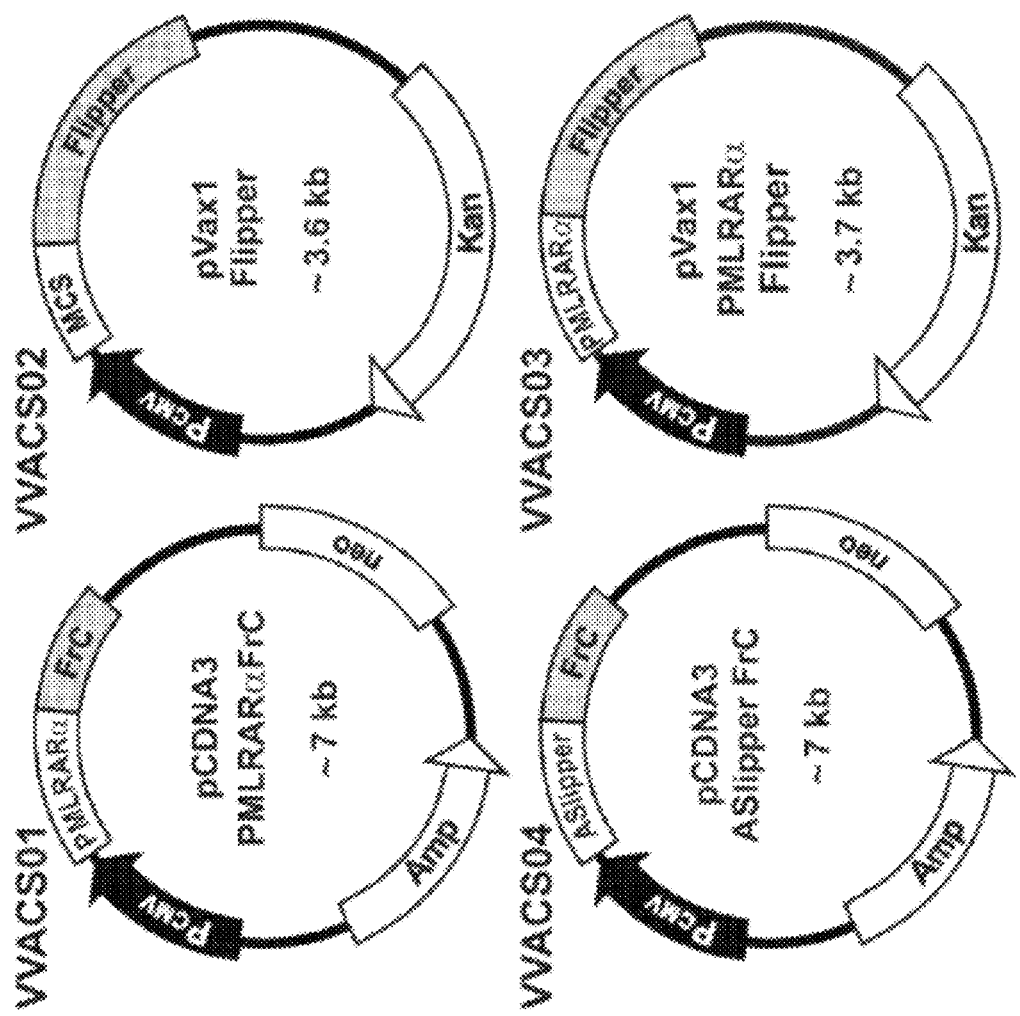

FIG. 10 represents maps of the VVACS plasmids.

Figure 11:
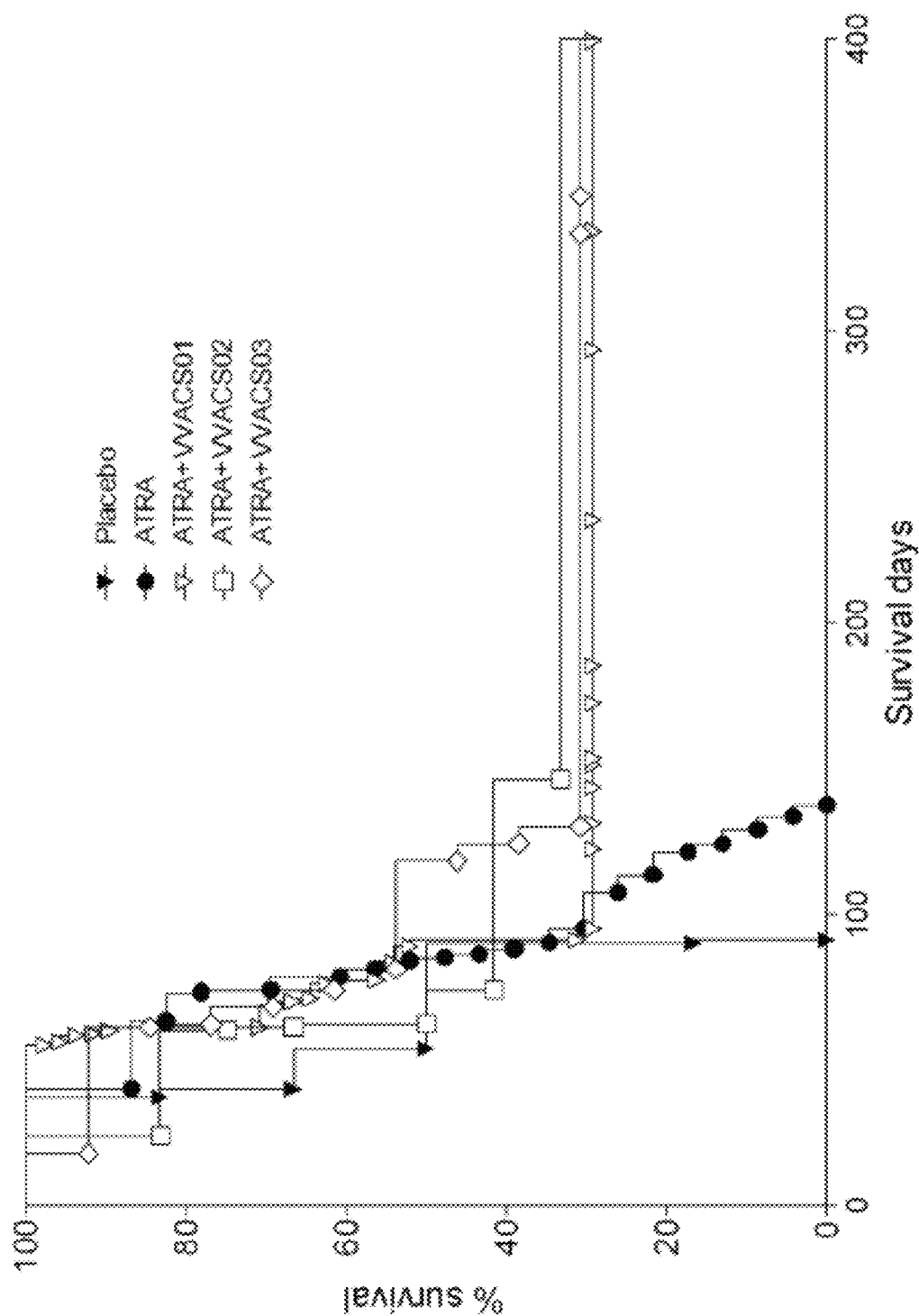
Figure 12:
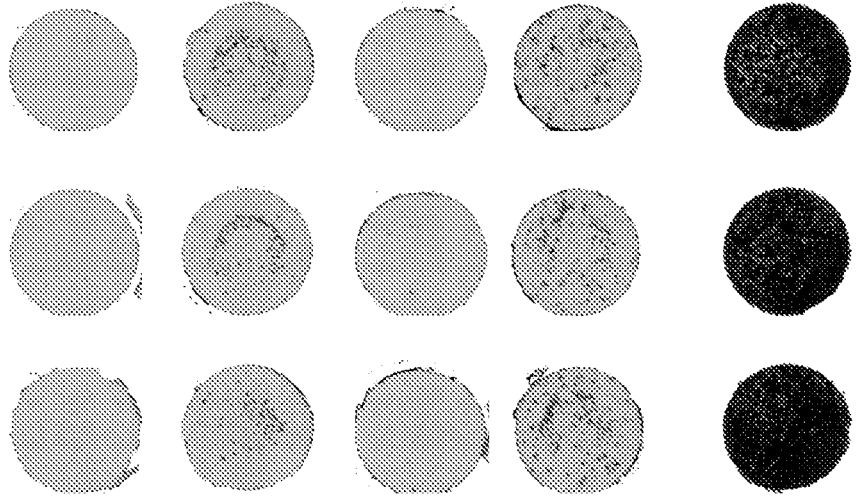

FIG. 11 shows the effect of different VVACS products (VVACS 01 & VVACS 02 & VVACS 03) plus ATRA in an AML mouse model FIG. 12 shows that DNA vaccination with VVCAS02 DNA results in specific T cell response. Elispot assay show Increase in IFNg.

Figure 13:
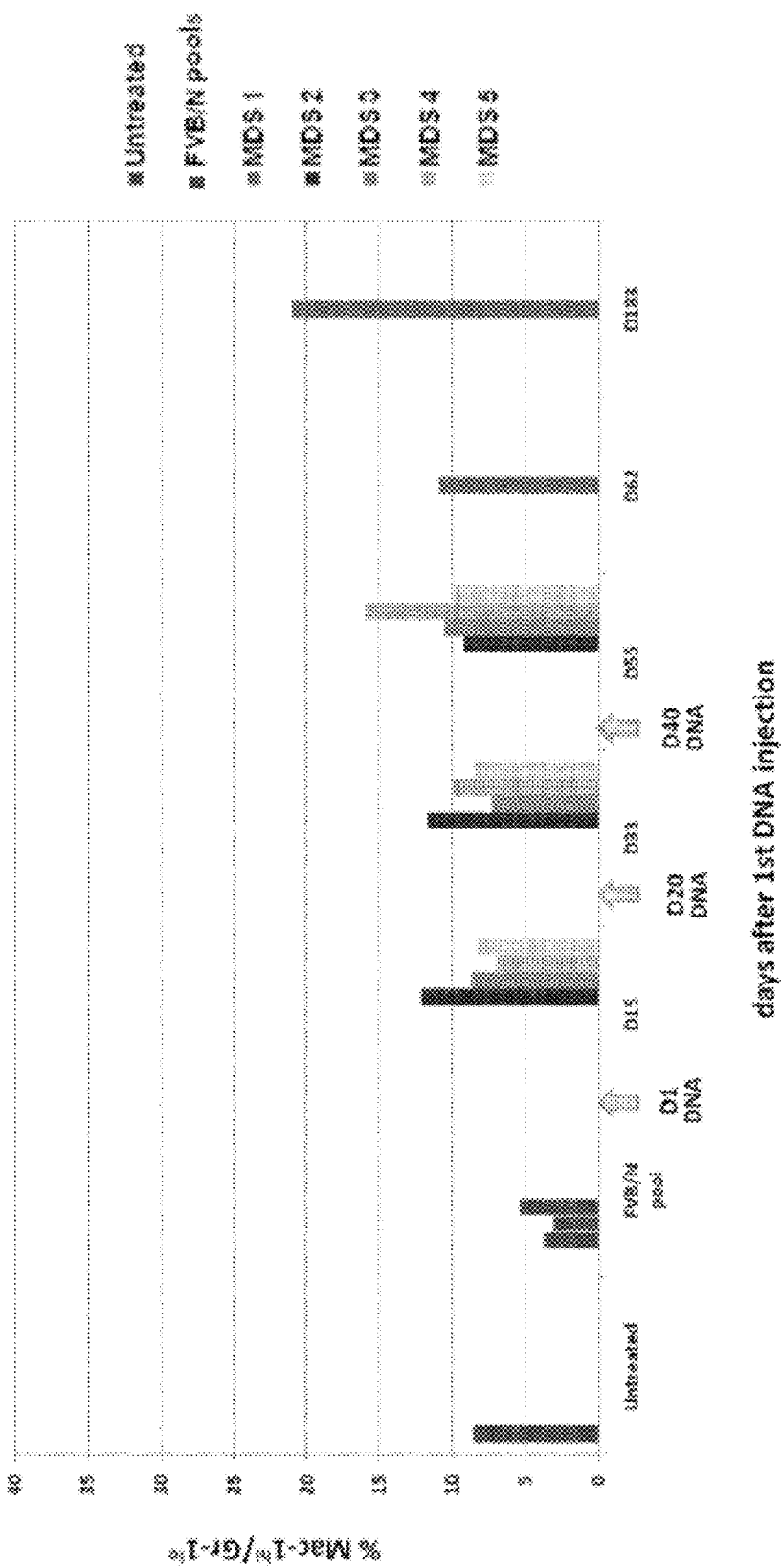

FIG. 13 shows that DNA Vaccination with VVCAS02 maintains stable disease.

DESCRIPTION OF THE SEQUENCES

SEQ ID NO: 1 shows the sequence of a KanAS nucleic acid comprising a sequence complementary to a fragment of the sequence coding for the kanamycin resistance protein.

SEQ ID NO: 2 shows the sequence of a KanAS nucleic acid comprising a sequence complementary to a fragment of the sequence coding for the kanamycin resistance protein and further comprising a sequence complementary to a fragment of the pVax plasmid.

SEQ ID NO: 3 shows the sequence of a PML-RARα-KanAS nucleic acid comprising a sequence encoding the PML-RARα antigen and a sequence complementary to a fragment of the sequence coding for the kanamycin resistance protein.

SEQ ID NO: 4 shows the sequence of a PML-RARα-KanAS nucleic acid comprising a sequence encoding the PML-RARα antigen, a sequence complementary to a fragment of the sequence coding for the kanamycin resistance protein, and a sequence complementary to a fragment of the pVax plasmid.

SEQ ID NO: 5 shows the sequence encoding the PML-RARα antigen.

SEQ ID NO: 6 shows the sequence of PML-RARαAS.

SEQ ID NO: 7 shows a fragment of the pVax14 plasmid.

SEQ ID NO: 8 shows a fragment of the pVax15 plasmid.

SEQ ID NO: 9 shows the sequence of an empty pVax1 vector.

SEQ ID Nos. 10-13 show the primers used for constructing the pVax14 plasmid.

SEQ ID Nos. 14-15 show the primers used for constructing the pVax15 plasmid.

SEQ ID NO: 16 shows the FrC sequence.

SEQ ID NO: 17 shows the complete sequence of the pVax14 plasmid. The flipper region comprises the KanAS sequence of SEQ ID NO: 2.

SEQ ID Nos. 18-23 show the sequences of immunogenic polypeptides.

EXAMPLES

Example 1

DNA Constructs

Five DNA constructs were used:
- the pCDNA₃PML-RARαFrC construct (also referred to as VVACS01), which is described in Example 1b, from page 18, line 12, to page 19, line 2 of WO 03/090778.
- the pCDNA₃PML-RARαASFrC construct (also referred to as VVACS04), which is described in Example 1b, page 19, lines 4-15 of WO 03/090778.
- the pVaxKanAS construct (also referred to as pVax14 or VVACS02), which was generated by cloning of a nucleic acid consisting of the sequence of SEQ ID NO: 1 into the pVax1 vector.
- the pVaxPML-RARαKanAS construct (also referred to as pVax15 or VVACS03), which was generated by cloning the sequence encoding the PML-RARα tumor antigen into pVax14.
- the pVaxPML-RARαFrC construct, which was generated by cloning PML-RARαFrC into the pVax1 vector.

pVax14 (pVaxKanAS or VVACS02) was constructed by PCR amplification of pVax1 with the following pairs of primers: a pair of primers of SEQ ID Nos. 10 and 11, and a pair of primer of SEQ ID Nos. 12 and 13. NotI and BamHI were used as cloning sites.

pVax15 (pVaxPML-RARαKanAS or VVACS03) was constructed by amplifying LeaderPML-RAR105 bp sequences from pCDNA₃PML-RARFrC using the primers of SEQ ID Nos. 14 and 15. The amplified fragment was cloned into pVax14 using the HindIII and BamHI cloning sites.

pCDNA₃PML-RARαFrC (VVACS01) and pVaxPML-RARαKanAS (VVACS03) were transiently transfected in COS cells. RQ-PCR experiments demonstrated that PML-RARα is expressed with both constructs.

Example 2

KanAS Extends Lifespan in an APL Mouse Model

The effect of different DNA constructs on an APL mouse model was studied using the protocol disclosed in Padua et al. (2003, Nature Medicine 9:1413-1417). Briefly, $10^4$ APL cells were injected to FVB/N mice. Then an ATRA pellet, which releases 5 mg/day of ATRA for 21 days, was introduced behind the neck of the mice with a trochar. DNA (2×50 micrograms of plasmid) was injected the day after introducing the ATRA pellet, and every 20 days for a total of three injections. The following DNA constructs were injected to the mice:

the pVaxKanAS construct, also referred to as pVax14;
the pCDNA$_3$PML-RARαFrC construct (VVACS01);
the pVaxPML-RARαFrC construct; and
the pCDNA$_3$PML-RARαASFrC construct (VVACS04).

A pellet purchased from the manufacturer of the ATRA pellet (Innovative Research, Sarasota, USA) was used as a placebo.

The mice were followed for two years and Kaplan-Meier curves were constructed.

The results are shown on FIG. 2 and in Table 1 hereinbelow. The log-rank (Mantel-Cox) and general Wilcoxon tests were applied to the Kaplan-Meier curves. Both statistical tests led to identical conclusions in terms of significance.

TABLE 1

|  | log-rank (Mantel-Cox) | | general Wilcoxon | |
|---|---|---|---|---|
|  | Chi-2 value | p value | Chi-2 value | p value |
| ATRA V.S. ATRA + pCDNA$_3$PML-RARαASFrC | 8.7257E+00 | 3.1375E−03  $p < 0.005$ | 7.1234E+00 | 7.6086E−03  $p < 0.01$ |
| ATRA V.S. ATRA + pCDNA$_3$PML-RARαFrC | 1.7729E+01 | 2.5473E−05  $p < 0.0001$ | 1.0263E+01 | 1.3571E−03  $p < 0.005$ |
| ATRA V.S. ATRA + pVaxPML-RARαFrC | 5.0145E+00 | 2.5136E−02  $p < 0.05$ | 5.1840E+00 | 2.2796E−02  $p < 0.05$ |
| ATRA V.S. ATRA + pVaxKanAS | 6.5927E+00 | 1.0240E−02  $p < 0.05$ | 2.3055E+00 | 1.2892E−01  n.s. |
| ATRA V.S. placebo | 6.0018E+01 | 9.3994E−15  $p < 0.0001$ | 5.1827E+01 | 6.0611E−13  $p < 0.0001$ |
| ATRA V.S. placebo + DNA | 8.7059E+00 | 3.1718E−03  $p < 0.005$ | 1.6318E+01 | 5.3547E−05  $p < 0.0001$ |
| ATRA + pCDNA$_3$PML-RARαASFrC V.S. ATRA + pCDNA$_3$PML-RARαFrC | 2.9314E−02 | 8.6406E−01  n.s. | 7.4390E−03 | 9.3127E−01  n.s. |
| ATRA + pCDNA$_3$PML-RARαASFrC V.S. ATRA + pVaxPML-RARαFrC | 2.3666E+00 | 1.2395E−01  n.s. | 1.0271E+00 | 3.1085E−01  n.s. |
| ATRA + pCDNA$_3$PML-RARαASFrC V.S. ATRA + pVaxKanAS | 6.0339E−05 | 9.9380E−01  n.s. | 8.7577E−02 | 7.6728E−01  n.s. |
| ATRA + pCDNA$_3$PML-RARαASFrC V.S. placebo | 3.1948E+01 | 1.5838E−08  $p < 0.0001$ | 2.4578E+01 | 7.1365E−07  $p < 0.0001$ |
| ATRA + pCDNA$_3$PML-RARαASFrC V.S. placebo + DNA | 1.3354E+01 | 2.5792E−04  $p < 0.0005$ | 1.3575E+01 | 2.2917E−04  $p < 0.0005$ |
| ATRA + pCDNA$_3$PML-RARαFrC V.S. ATRA + pVaxPML-RARαFrC | 3.8212E+00 | 5.0608E−02  n.s. | 1.0797E+00 | 2.9876E−01  n.s. |
| ATRA + pCDNA$_3$PML-RARαFrC V.S. ATRA + pVaxKanAS | 1.3756E−02 | 9.0663E−01  n.s. | 2.5419E−01 | 6.1414E−01  n.s. |
| ATRA + pCDNA$_3$PML-RARαFrC V.S. placebo | 7.3553E+01 | 9.7951E−18  $p < 0.0001$ | 6.4450E+01 | 9.9035E−16  $p < 0.0001$ |

TABLE 1-continued

|  | log-rank (Mantel-Cox) | | general Wilcoxon | |
| --- | --- | --- | --- | --- |
|  | Chi-2 value | p value | Chi-2 value | p value |
| ATRA + pCDNA$_3$PML-RARαFrC V.S. placebo + DNA | 2.9433E+01 | 5.7887E−08  p < 0.0001 | 3.0640E+01 | 3.1065E−08  p < 0.0001 |
| ATRA + pVaxPML-RARαFrC V.S. ATRA + pVaxKanAS | 2.2960E+00 | 1.2971E−01  n.s. | 5.2380E−01 | 4.6923E−01  n.s. |
| ATRA + pVaxPML-RARαFrC V.S. placebo | 2.6830E+01 | 2.2214E−07  p < 0.0001 | 2.1359E+01 | 3.8082E−06  p < 0.0001 |
| ATRA + pVaxPML-RARαFrC V.S. placebo + DNA | 1.0216E+01 | 1.3921E−03  p < 0.005 | 1.0704E+01 | 1.0688E−03  p < 0.005 |
| ATRA + pVaxKanAS V.S. placebo | 1.7202E+01 | 3.3607E−05  p < 0.0001 | 1.2455E+01 | 4.1695E−04  p < 0.0005 |
| ATRA + pVaxKanAS V.S. placebo + DNA | 7.8950E+00 | 4.9572E−03  p < 0.005 | 6.2853E+00 | 1.2174E−02  p < 0.05 |
| placebo V.S. placebo + DNA | 4.0649E+00 | 4.3783E−02  p < 0.05 | 4.1371E+00 | 4.1953E−02  p < 0.05 |

Thus the pVaxKanAS construct, administered in combination with ATRA, has a protective effect in the APL mouse model. About 40% of the mice were rescued from death. This protective effect is comparable with the protective effect of the pCDNA$_3$PML-RARαFrC construct. On the other hand, the protective effect of the pVaxKanAS construct is significantly different from ATRA alone (p=<0.05 for ATRA versus ATRA+pVaxKanAS).

A separate experiment was carried out to study the effect of the PML-RARαKanAS construct (also referred to as pVax15). The protocol was the same as above, except from the fact that the APL cells used for this experiment were of higher passage and more aggressive, and that the mice were followed for nine months.

The results are shown on FIG. 3 and in Table 2 herebelow.

TABLE 2

|  | log-rank (Mantel-Cox) | |
| --- | --- | --- |
|  | Chi-2 value | p value |
| ATRA V.S. ATRA + pCDNA$_3$PML-RARαFrC | 9.883 | 0.0017 |
| ATRA V.S. ATRA + pVAXKanASFrC | 11.080 | 0.0009 |
| ATRA + pCDNA$_3$PML-RARαFrC V.S. ATRA + pVAXKanAS | 0.004 | 0.9482 |

The PML-RARαKanAS construct also has a protective effect compared to ATRA alone (p=0.0009). The PML-RARαKanAS construct is at least as effective as the pCDNA$_3$PML-RARαFrC construct.

Example 3

KanAS and PMLRARαASFrC Extends Lifespan in an MDS Mouse Model

The MDS mouse model described in Omidvar et al. (2007, Cancer Res. 67:11657-67) was used to study the effect of KanAS on MDS. This mouse model is based on the use of mice bearing mutant NRAS with BCL-2, which are followed until they have a reduced platelet count indicative of thrombocytopenia and imminent death.

The vaccination protocol was as follows: 2×50 micrograms of DNA were administered day after diagnosis of diagnosis (day 0), which corresponded to the day on which the peripheral blood platelet count fell below normal (<$10^5$/microliter). On day 20 and on day 40, 2×50 micrograms of DNA were injected again.

A first experiment was carried out with six mice treated with pVaxKanAS (VVACS02). As shown on FIG. 4, KanAS alone extends lifespan of the mice compared with the untreated group (p=0.003).

A second experiment was carried out with ten mice treated with pVaxKanAS and sixteen mice treated with pCDNA$_3$PML-RARαFrC (VVACS04). This experiment, the results of which are shown on FIG. 5, confirmed the results obtained in the frame of the previous experiment.

A third experiment was carried out in order to study the effect of combined administration of ATRA and pCDNA3PMLRARASFrC or VVACS04 (FIG. 6). The mice were divided into four groups:
  mice treated with pCDNA3PMLRARαASFrC;
  mice treated with ATRA;
  mice treated with ATRA and pcDNA3PMLRARαASFrC; and
  untreated mice.

The mice were followed until disease onset when the platelet counts dropped below $10^5$/microliter. The mice were treated with pellets releasing 10 mg of ATRA for 21 days (Innovative Research, Sarasota, USA). The next day the mice were treated with 2×50 micrograms of DNA, and then at 20 day intervals on two occasions, giving a total of 300 micrograms per mouse.

In conclusion, DNA constructs comprising KanAS are highly efficient in DNA vaccination, either alone or combined with a non-immunosuppressor inducer of tumor cell apoptosis. Such KanAS constructs can be used as DNA vaccines, for example to protect APL and MDS patients from either relapse or disease progression.

Example 4

Relapse of the Disease in an MDS Mouse Model

Transgenic mice bearing mutant NRAS with BCL-2 mice will never be cured, and will necessarily relapse and die. Therefore, experiments were carried out in order to determine how long the immunity induced upon administration of DNA constructs comprising KanAS can last for. To this end, the CD4$^+$CD44$^{hi}$CD62L$^{lo}$ profile (FIG. 7) and the Mac-2$^{hi}$/Gr1$^{lo}$ profile (FIG. 8) of MDS mice treated with pVaxKanAS (pVax14, VVACS02) were analyzed. The relapse of the disease is tracked by an increase in the Mac1$^{hi}$/Gr1$^{lo}$ population, which is a marker of diseased leukaemic stem cell progenitors.

The mice were followed for disease progression by measuring blood counts. When the platelets dropped to below 10$^5$/microliter, the mice were recruited to trial and vaccinated with 2×50 micrograms of pVax14 (pVaxKanAS) DNA. At 20 day intervals, the injections with DNA were repeated. Thus the last injection was made on day 40.

After the 3rd course of injection the mice were followed for disease progression. More specifically, the Mac1/Gr1 status was studied by flow cytometry (FIG. 8) and presence of memory T-cells as marked by CD44$^{hi}$ and CD62L$^{lo}$ (FIG. 7). Relapse of the disease appeared to occur around day 150.

It was found that MDS mice treated with pVaxKanAS alone had a 3-fold increased memory T-cells compared to wild type FVB/N mice. Furthermore, the leukaemic initiating cell population was reduced upon treatment with pVaxKanAS (approximately 25% in untreated mice versus approximately 10% in treated mice). These results confirm that DNA constructs comprising KanAS are efficient for treating cancer patients.

Example 5

Effect of DNA Constructs Comprising KanAS in an AML Mouse Model

The effect of different constructs, comprising or not a KanAS nucleic acid, was assessed in a mouse model of AML.

The constructs are shown on FIG. 10. The constructs referred to as VVACS02 and VVACS04 comprise a KanAS nucleic acid according to the invention in the "Flipper" region. More specifically, VVACS02 is the vector referred to as pVax14 hereabove. The sequence of this vector is shown as SEQ ID NO: 17.

Figure 1:
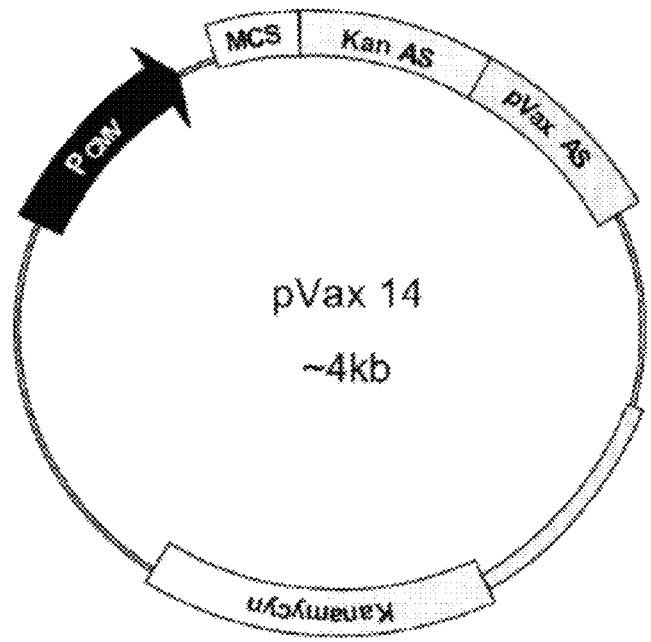
FIG. 1 depicts the pVax14 and the pVax15 plasmids, which comprise KanAS nucleic acids according to the invention. pVax14 comprises a KanAS nucleic acid of SEQ ID NO: 1, and pVax15 comprises a PML-RARαKanAS nucleic acid of SEQ ID NO: 3.
Figure 1:
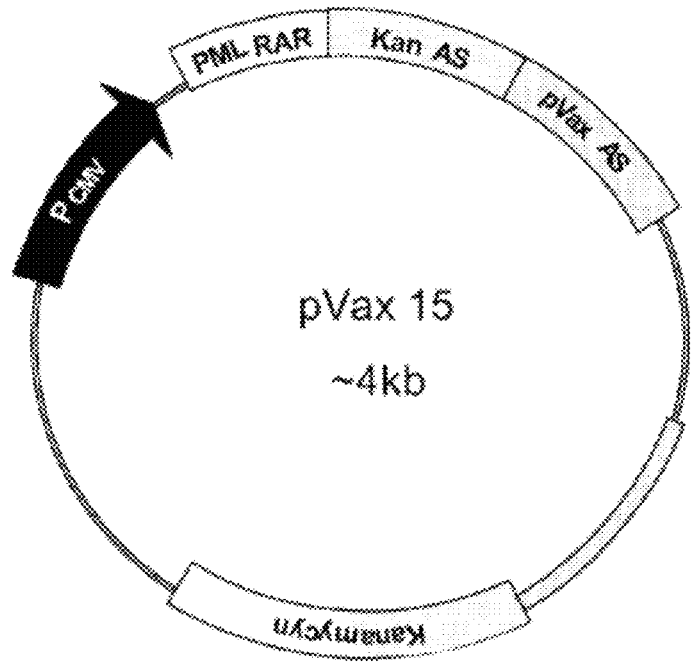
Figure 2:
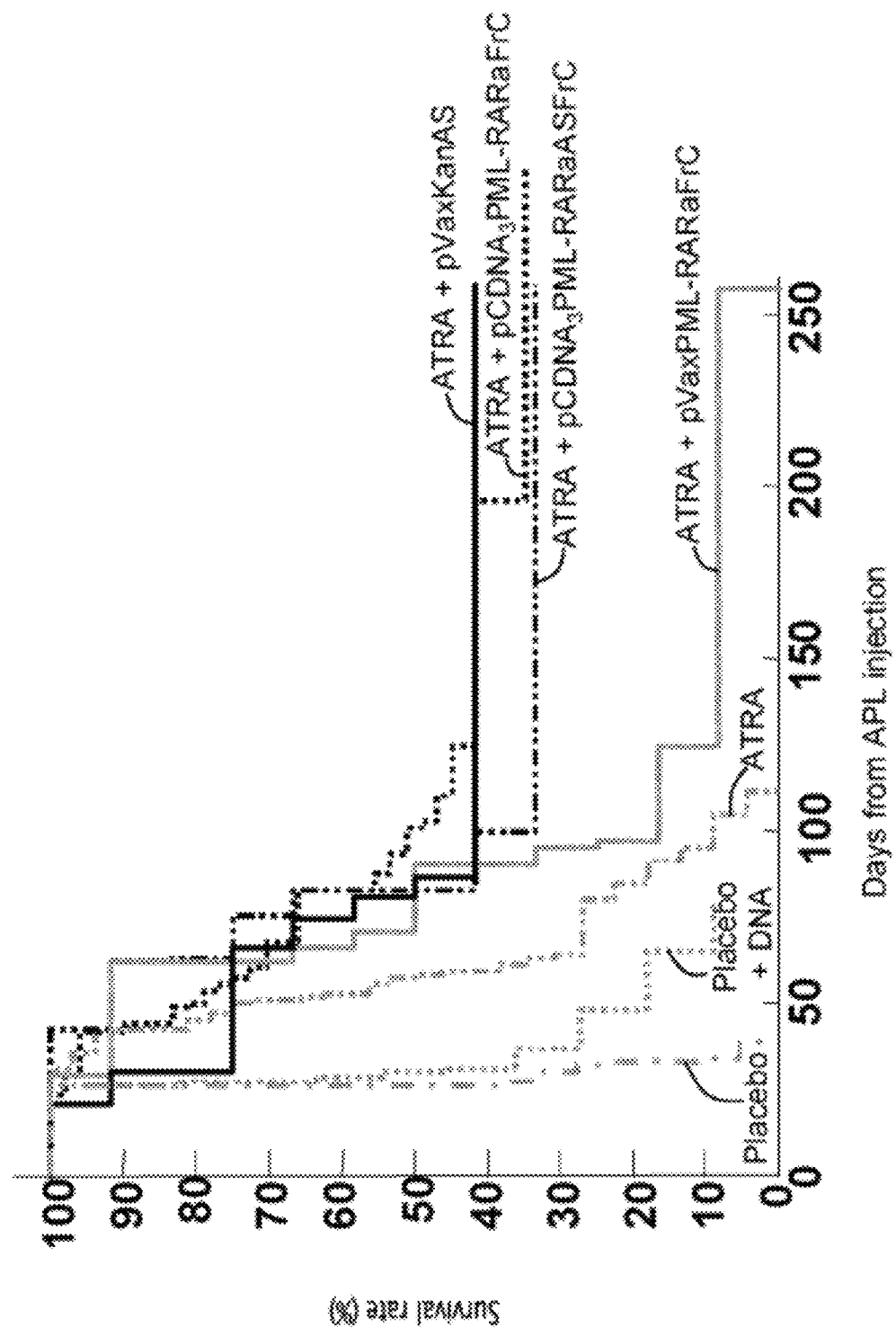
FIG. 2 shows that the pVax14 nucleic acid, which comprises the KanAS nucleic acid of SEQ ID NO: 1, extends lifespan in an APL (acute promyelocytic leukaemia) mouse model. See FIG. 10 for maps of plasmids. Row 1: ATRA+ pVaxKanAS (n=12) (PVax14, VVACS02); Row 2: ATRA+ pCDNA₃PML-RARαFrC (n=48) (VVACS01); Row 3.

FIGS. 2 and 11 show that the combination of ATRA and of DNA constructs comprising KanAS extends lifespan of the mice.

The Elispot assay (Furugaki et al., Blood. 2010; 115:653-6) was used for determining whether DNA vaccination with VVCAS02 (pVax14 or pVaxKanAS) DNA results in specific T cell response. The results are shown on FIG. 12.

As shown on FIG. 13, DNA vaccination with VVACS02 (pVax14 or pVaxKanAS) results in a stable disease.

The fact that DNA vaccination with VVACS02 (pVax14 or pVaxKanAS) results in a stable disease was further studied by quantifying ERK using a Firefly™ Instrument (Cell Biosciences), as described in Fan et al. (Nat Med. 2009; 15:566-71). The results are shown in Tables 3 and 4 below.

TABLE 3

ERK ½ Quantitation in spleen

| Cell Line/Treatment | ID Number | % ppERK1 | % pERK1 | % ERK1 | % ppERK2 | % pERK2 | % ERK2 |
|---|---|---|---|---|---|---|---|
| FVBN | 9140 | 16.32 | 74.29 | 9.39 | ND | 9.09 | 90.91 |
| RAS | 6951 | 21.47 | 64.33 | 14.20 | ND | 17.42 | 82.58 |
|  | 6953 | 20.94 | 60.66 | 18.40 | ND | 17.65 | 82.35 |
| BCL2 | 7565 | 13.47 | 66.33 | 20.20 | ND | 15.98 | 84.02 |
|  | 7810 | 10.33 | 77.02 | 12.65 | ND | 13.81 | 86.19 |
| MMTV/TBCL2/NRAS | 7240 | 14.38 | 69.06 | 16.56 | ND | 20.25 | 79.75 |
|  | 8111 | 22.21 | 65.37 | 12.41 | ND | 24.76 | 75.24 |

TABLE 4

ERK ½ Quantitation in PBL

| Treatment | ID Number | % ppERK1 | % pERK1 | % ERK1 | % ppERK2 | % pERK2 | % ERK2 |
|---|---|---|---|---|---|---|---|
| DNA Vaccine | 9275 | 2.6 | 68.5 | 28.9 | ND | 13.5 | 86.5 |
|  | 9282 | 2.7 | 73.8 | 23.5 | ND | 15.6 | 84.4 |
|  | 9400 | 1.3 | 77.2 | 21.5 | ND | 18.0 | 82.0 |
|  | 9451 | 4.2 | 74.3 | 21.5 | ND | 10.3 | 89.7 |

The mechanism of action of VVACS02 (pVax14 or pVaxKanAS) was characterized.

Firstly, memory T cells in FVN control mice and in 4 MDS-AML mice was assessed at different days after treatment with VVACS02 and ATRA. An increase in memory T-cell population—CD4+ CD44hi CD62Llo was observed after 2$^{nd}$ DNA vaccination (data not shown). In addition, memory T-cells were maintained at high levels about 4-5 months after the last DNA injection (data not shown).

Secondly, expression of MyD88 (a gene downstream of the TLRs) was assessed in (i) control FVBN mice, (ii) two MDS-AML mice treated with VVACS02 and ATRA at day 113 or at day 142, and (iii) one MDS-AML mouse treated with another drug. In the mouse treated with VVACS02 at day 113, an increased expression of MyD88 and an activation of TLRs was observed (data not shown). In addition, there was a basal expression about 3.5 months after the last DNA injection. This effect was not observed for the other mice. This result suggests Toll-like receptors play a role in the beneficial effect of VVACS02.

In summary, the experimental data presented in Example 5 demonstrate that VVACS02 gives rise to stable disease in the MDS model. It also gives rise to appropriate immune responses. These results suggest that that the mechanism by which VVACS02 is acting is as a DNA adjuvant engaging the Toll-like receptors, as shown by measuring the downstream molecule MYD88 whose expression is upregulated, in contrast to treatments without DNA adjuvant such as ATRA alone.

Example 6

Effect of the Combination of a DNA Construct Comprising KanAS, ATRA and 5-azacytidine in a MDS Mouse Model The MDS mouse model described in Omidvar et al. (2007, Cancer Res. 67:11657-67) was used to study the effect of the combination of KanAS, ATRA and 5-azacytidine on MDS.

100 microliters of 1 mg/ml solution of 5-Azacytidine was injected IP to the mice on the day of diagnosis and then on Mondays, Wednesdays and Fridays until death of the mice.

ATRA was administered through a 10 mg 21 day release pellet

The vaccination protocol was as follows: 100 micrograms of DNA (VVACS02 or pVax14 or pVaxKanAS) were administered day after diagnosis of diagnosis (day 0), which corresponded to the day on which the peripheral blood platelet count fell below normal (<$10^5$/microliter). On day 20 and on day 40, 2×50 micrograms of DNA were injected again.

The mice were randomly divided into four groups after twelve 5-azacytidine injections:

5-Azacytidine (n=5)
5-azacytidine+ATRA (n=4)
5-azacytidine+VVACS02 DNA (n=4)
5-azacytidine+ATRA+VVACS02 DNA (n=4)

The results are shown in Table 5 below.

TABLE 5

| Treatment | Days alive from treatment |
|---|---|
| 5-azacytidine | |
| 1 | 33 |
| 2 | Alive on 24 Mar. 2010 (112 days) |
| 3 | 72 |
| 4 | Alive on 24 Mar. 2010 (75 days) |
| 5 | 37 |
| 5-azacytidine + ATRA | |
| 1 | Alive on 24 Mar. 2010 (112 days) |
| 2 | Alive on 24 Mar. 2010 (75 days) |
| 3 | 59 |
| 4 | 41 |
| 5-azacytidine + VVACS02 DNA | |
| 1 | 100 |
| 2 | 73 |
| 3 | 48 |
| 4 | Alive on 24 Mar. 2010 (42 days) |
| 5-azacytidine + ATRA + VVACS02DNA | |
| 1 | Alive on 24 Mar. 2010 (112 days) |
| 2 | Alive on 24 Mar. 2010 (103 days) |
| 3 | Alive on 24 Mar. 2010 (75 days) |
| 4 | Alive on 24 Mar. 2010 (75 days) |

The combination of KanAS, ATRA and 5-azacytidine thus extends lifespan in an MDS mouse model.

The invention claimed is:

1. An isolated nucleic acid comprising:
   an antisense sequence consisting of a sequence complementary to a fragment of a sequence coding for a kanamycin resistance protein;
   and a sequence which encodes an immunogenic polypeptide;
   wherein the fragment is at least 100 nucleotides and at most 500 nucleotides in length; wherein the antisense sequence encodes at least one immunogenic polypeptide selected from the group consisting of a polypeptide of sequence SEQ ID NO: 18 and a polypeptide of sequence SEQ ID NO: 19; wherein the sequence coding for the kanamycin resistance protein has a sequence consisting of nucleotides 1226 to 2020 of SEQ ID NO: 9; and wherein said antisense sequence is under control of a mammalian promoter allowing its transcription.

2. An isolated nucleic acid according to claim 1, wherein said antisense sequence consists of a sequence selected from the group consisting of:
   a) sequence SEQ ID NO: 1;
   b) a sequence at least 80% identical to SEQ ID NO: 1; and
   c) a fragment of at least 100 consecutive nucleotides of SEQ ID NO: 1.

3. A nucleic acid according to claim 1, wherein said sequence which encodes an immunogenic polypeptide encodes a tumor antigen.

4. A nucleic acid according to claim 3, wherein said sequence which encodes a tumor antigen is at least 80% identical to the PML-RARα sequence of SEQ ID NO: 5.

5. A nucleic acid according to claim 1, wherein said nucleic acid comprises a sequence selected from the group consisting of:
   a) the sequence SEQ ID NO: 2, SEQ ID NO: 3 or SEQ ID NO: 4;
   b) a sequence at least 80% identical to SEQ ID NO: 2, SEQ ID NO: 3 or SEQ ID NO: 4; and
   c) a fragment of at least 100 consecutive nucleotides of SEQ ID NO: 2, SEQ ID NO: 3 or SEQ ID NO: 4.

6. A method for eliciting an immune response, comprising administering an effective amount of a nucleic acid according to claim 1 to a patient in need thereof, wherein said nucleic acid comprises an antisense sequence encoding at least one immunogenic polypeptide having the capacity to elicit an immune response.

7. The method of claim 6, wherein the method further comprises the simultaneous or sequential administration of a non-immunosuppressive inducer of tumor cell apoptosis.

8. The method of claim 6, wherein said patient suffers or is susceptible to suffering from a blood cancer selected from the group consisting of lymphoid leukaemia, myeloid leukaemia, acute promyelocytic leukaemia (APL), myelodysplastic syndrome (MDS), acute myeloid leukaemia (AML), myelomonocytic leukaemia (CMML), chronic lymphocytic leukaemia (CLL), chronic myelogenous leukaemia (CML), childhood acute lymphoblastic leukaemia (ALL), Hodgkin lymphoma (HL), non-Hodgkin lymphoma (NHL) and multiple myeloma (MM).

9. The method of claim 6, wherein said patient suffers or is susceptible to suffering from a solid tumor selected from the group consisting of a carcinoma, an adenocarcinoma, a sarcoma, a melanoma, a mesothelioma and a blastoma.

10. A vector comprising the nucleic acid of claim 1.

11. A pharmaceutical composition comprising:
    (i) a nucleic acid according to claim 1 or a vector according to claim 10;
    (ii) a physiologically acceptable carrier; and, optionally,
    (iii) a non-immunosuppressive inducer of tumor cell apoptosis.

12. A pharmaceutical composition according to claim 11, further comprising a non-immunosuppressive inducer of tumor cell apoptosis.

13. A combination of:
    (i) a first pharmaceutical composition comprising a nucleic acid according to claim 1 or a vector according to claim 10 in a physiologically acceptable carrier; and
    (ii) a second pharmaceutical composition comprising a non-immunosuppressive inducer of tumor cell apoptosis in a physiologically acceptable carrier.

14. The method of claim 7, wherein said non-immunosuppressive inducer of tumor cell apoptosis is a retinoid compound or an arsenic-related compound.

15. A pharmaceutical composition according to claim 12, wherein said non-immunosuppressive inducer of tumor cell apoptosis is a retinoid compound or an arsenic-related compound.

16. A combination according to claim 13, wherein said non-immunosuppressive inducer of tumor cell apoptosis is a retinoid compound or an arsenic-related compound.

17. The method of claim 14, wherein said retinoid compound is ATRA.

18. A pharmaceutical composition according to claim 15, wherein said retinoid compound is ATRA.

19. A combination according to claim 16, wherein said retinoid compound is ATRA.

20. An isolated nucleic acid comprising an antisense sequence consisting of a sequence complementary to a fragment of a sequence coding for a kanamycin resistance protein, wherein the fragment is at least 100 nucleotides and at most 500 nucleotides in length, wherein said antisense sequence encodes at least one immunogenic polypeptide selected from the group consisting of a polypeptide of sequence SEQ ID NO: 18 and a polypeptide of sequence SEQ ID NO: 19, wherein said nucleic acid comprises a sequence selected from the group consisting of:
    a) the sequence SEQ ID NO: 2 and
    b) a sequence at least 85% identical to SEQ ID NO: 2;
    and wherein said antisense sequence is under control of a mammalian promoter allowing its transcription.

21. A nucleic acid according to claim 20, wherein said nucleic acid further comprises a sequence which encodes a tumor antigen.

22. A nucleic acid according to claim 21, wherein said sequence which encodes a tumor antigen is at least 80% identical to the PML-RARα sequence of SEQ ID NO: 5.

23. A vector comprising the nucleic acid of claim 20.

24. A pharmaceutical composition comprising:
    (i) a nucleic acid according to claim 20 or a vector according to claim 23;
    (ii) a physiologically acceptable carrier; and, optionally,
    (iii) a non-immunosuppressive inducer of tumor cell apoptosis.

25. A pharmaceutical composition according to claim 24, further comprising a non-immunosuppressive inducer of tumor cell apoptosis.

26. A pharmaceutical composition according to claim 25, wherein said non-immunosuppressive inducer of tumor cell apoptosis is a retinoid compound or an arsenic-related compound.

27. A pharmaceutical composition according to claim 26, wherein said retinoid compound is ATRA.

28. A combination of:
(i) a first pharmaceutical composition comprising a nucleic acid according to claim 20 or a vector according to claim 23 in a physiologically acceptable carrier; and
(ii) a second pharmaceutical composition comprising a non-immunosuppressive inducer of tumor cell apoptosis in a physiologically acceptable carrier.

29. A combination according to claim 28, wherein said non-immunosuppressive inducer of tumor cell apoptosis is a retinoid compound or an arsenic-related compound.

30. A combination according to claim 29, wherein said retinoid compound is ATRA.

31. An isolated nucleic acid according to claim 1, further comprising a sequence which encodes an immunogenic polypeptide having a sequence at least 85% identical to sequence SEQ ID NO: 22.

32. An isolated nucleic acid comprising:
an antisense sequence consisting of a sequence complementary to a fragment of a sequence coding for a kanamycin resistance protein; and
a sequence which encodes an immunogenic polypeptide,
wherein the fragment is at least 100 nucleotides and at most 500 nucleotides in length, wherein the antisense sequence encodes at least one immunogenic polypeptide selected from the group consisting of a polypeptide of sequence SEQ ID NO: 18 and a polypeptide of sequence SEQ ID NO: 19,
wherein the sequence coding for the kanamycin resistance protein consists of a sequence at least 85% identical to nucleotides 1226 to 2020 of SEQ ID NO: 9, and
wherein said antisense sequence is under control of a mammalian promoter allowing its transcription.

33. An isolated nucleic acid comprising:
an antisense sequence consisting of a sequence complementary to a fragment of a sequence coding for a kanamycin resistance protein; and
a sequence which encodes an immunogenic polypeptide,
wherein the fragment is at least 100 nucleotides and at most 500 nucleotides in length, wherein the antisense sequence encodes at least one immunogenic polypeptide selected from the group consisting of a polypeptide of a sequence at least 85% identical to sequence SEQ ID NO: 18 and a polypeptide of a sequence at least 85% identical to sequence SEQ ID NO: 19,
wherein the sequence coding for the kanamycin resistance protein consists of a sequence at least 85% identical to nucleotides 1226 to 2020 of SEQ ID NO: 9, and
wherein said antisense sequence is under control of a mammalian promoter allowing its transcription.

34. An isolated nucleic acid according to claim 20, wherein said nucleic acid comprises nucleotides 762 to 1587 of sequence SEQ ID NO: 17.

35. A method for eliciting an immune response, comprising administering an effective amount of a nucleic acid according to claim 20, 32 or 33 to a patient in need thereof, wherein said nucleic acid comprises an antisense sequence encoding at least one immunogenic polypeptide having the capacity to elicit an immune response.

* * * * *